(12) United States Patent
Vermot-Desroches et al.

(10) Patent No.: US 11,634,488 B2
(45) Date of Patent: Apr. 25, 2023

(54) TREATMENT OF B CELL MALIGNANCIES USING AFUCOSYLATED PRO-APOPTOTIC ANTI-CD19 ANTIBODIES IN COMBINATION WITH ANTI CD20 ANTIBODIES OR CHEMOTHERAPEUTICS

(71) Applicant: INTERNATIONAL—DRUG—DEVELOPMENT—BIOTECH, Lyons (FR)

(72) Inventors: Claudine Vermot-Desroches, Dardilly (FR); Chanthy Kong-Flohr, Pontcharra sur Turdine (FR); Marc Godinat, Tassin la Demi Lune (FR); Bruno Cavallini, Saint Germain au Mont d'Or (FR)

(73) Assignee: INTERNATIONAL—DRUG—DEVELOPMENT—BIOTECH, Lyons (FR)

( * ) Notice: Subject to any disclaimer, the term of this patent is extended or adjusted under 35 U.S.C. 154(b) by 243 days.

(21) Appl. No.: 16/630,351

(22) PCT Filed: Jul. 10, 2018

(86) PCT No.: PCT/EP2018/068672
§ 371 (c)(1),
(2) Date: Jan. 10, 2020

(87) PCT Pub. No.: WO2019/011918
PCT Pub. Date: Jan. 17, 2019

(65) Prior Publication Data
US 2022/0227862 A1 Jul. 21, 2022

(30) Foreign Application Priority Data

Jul. 10, 2017 (EP) .................................... 17305898

(51) Int. Cl.
*C07K 16/28* (2006.01)
*A61P 35/00* (2006.01)
*A61K 39/00* (2006.01)

(52) U.S. Cl.
CPC .......... *C07K 16/2803* (2013.01); *A61P 35/00* (2018.01); *C07K 16/2887* (2013.01); *A61K 2039/507* (2013.01); *C07K 2317/24* (2013.01); *C07K 2317/31* (2013.01); *C07K 2317/41* (2013.01); *C07K 2317/52* (2013.01); *C07K 2317/732* (2013.01)

(58) Field of Classification Search
CPC ........ A61K 2039/507; A61K 2039/505; A61K 31/475; A61K 39/39558; C07K 2317/24; C07K 2317/31; C07K 2317/41; C07K 2317/52; C07K 2317/732; C07K 2317/73; C07K 2317/734
See application file for complete search history.

(56) References Cited

U.S. PATENT DOCUMENTS

| | | |
|---|---|---|
| 4,554,101 A | 11/1985 | Hopp |
| 5,595,721 A | 1/1997 | Kaminski et al. |
| 5,736,137 A | 4/1998 | Anderson et al. |
| 5,843,398 A | 12/1998 | Kaminski et al. |
| 6,015,542 A | 1/2000 | Kaminski et al. |
| 6,090,365 A | 7/2000 | Kaminski et al. |
| 6,194,551 B1 | 2/2001 | Idusogie et al. |
| 6,242,195 B1 | 6/2001 | Idusogie et al. |
| 6,528,624 B1 | 2/2003 | Hikita et al. |
| 6,538,124 B1 | 3/2003 | Idusogie et al. |
| 6,737,056 B1 | 5/2004 | Presta et al. |
| 6,946,292 B2 | 9/2005 | Kanda et al. |
| 7,109,304 B2 | 9/2006 | Hansen et al. |
| 7,166,306 B2 | 1/2007 | Chen et al. |
| 7,183,387 B1 | 2/2007 | Presta et al. |
| 7,276,585 B2 | 10/2007 | Lazar et al. |
| 7,297,775 B2 | 11/2007 | Idusogie et al. |
| 7,335,742 B2 | 2/2008 | Presta |
| 7,355,008 B2 | 4/2008 | Stavenhagen et al. |
| 7,364,731 B2 | 4/2008 | Idusogie et al. |
| 7,416,727 B2 | 8/2008 | Presta |

(Continued)

FOREIGN PATENT DOCUMENTS

| | | |
|---|---|---|
| CN | 101534859 | 9/2009 |
| CN | 103360494 | 10/2013 |

(Continued)

OTHER PUBLICATIONS

Winkler, U., et al., "Cytokine-Release Syndrome in Patients with B-Cell Chronic Lymphocytic Leukemia and High Lymphocyte Counts After Treatment with an Anti-CD20 Monoclonal Antibody (Rituximab, IDEC-C2B8)", 1999, 9 pages, vol. 94, Blood.

Weng, Wen-Kai, et al., "Expression of Complement Inhibitors CD46, CD55, and CD59 on Tumor Cells does not Predict Clinical Outcome After Rituximab Treatment in Follicular Non-Hodgkin Lymphoma", 2001, 7 pages, vol. 98, Blood.

Wang, Z., et al., "Universal PCR Amplification of Mouse Immunoglobulin Gene Variable Regions: the Design of Degenerate Primers and an Assessment of the Effect of DNA Polymerase 3' to 5' Exonuclease Activity", 2000, pp. 167-177, vol. 233, Journal of Immunological Methods.

(Continued)

*Primary Examiner* — Nelson B Moseley, II
(74) *Attorney, Agent, or Firm* — B. Aaron Schulman, Esq.; Stites & Harbison, PLLC

(57) ABSTRACT

The invention relates to novel combination therapies involving anti-CD19 antibodies for the treatment of cancer B cells expressing CD19. One preferred method is where the anti-CD19 proapoptotic MAb or a Fc optimized proapototic humanized MAb. In the methods of the present invention some anti-CD20 agents such as Rituxan®, or chemodrugs such as vincristine may be used in combitherapy. The methods of the present invention reduce the levels of B CD19 positive, more particularly in all diffuse large B cells lymphoma (DLBCL) subtypes and in Follicular lymphomas (FL).

9 Claims, 21 Drawing Sheets
Specification includes a Sequence Listing.

(56) References Cited

U.S. PATENT DOCUMENTS

| | | |
|---|---|---|
| 7,425,619 B2 | 9/2008 | Koenig et al. |
| 7,425,620 B2 | 9/2008 | Koenig et al. |
| 7,462,352 B2 | 12/2008 | Hansen et al. |
| 7,632,497 B2 | 12/2009 | Stavenhagen et al. |
| 7,635,472 B2 | 12/2009 | Kufer et al. |
| 7,657,380 B2 | 2/2010 | Lazar et al. |
| 7,741,072 B2 | 6/2010 | Idusogie et al. |
| 7,786,270 B2 | 8/2010 | Johnson et al. |
| 7,960,512 B2 | 6/2011 | Stavenhagen et al. |
| 7,968,687 B2 | 6/2011 | McDonagh et al. |
| 8,003,774 B2 | 8/2011 | Stavenhagen et al. |
| 8,044,180 B2 | 10/2011 | Koenig et al. |
| 8,063,187 B2 | 11/2011 | Chu et al. |
| 8,188,231 B2 | 5/2012 | Lazar et al. |
| 8,192,737 B2 | 6/2012 | Stavenhagen et al. |
| 8,193,318 B2 | 6/2012 | Koenig et al. |
| 8,216,574 B2 | 7/2012 | Stavenhagen et al. |
| 8,216,579 B2 | 7/2012 | Johnson et al. |
| 8,217,147 B2 | 7/2012 | Stavenhagen |
| 8,242,252 B2 | 8/2012 | McDonagh et al. |
| 8,323,653 B2 | 12/2012 | Damschroder et al. |
| 8,445,645 B2 | 5/2013 | Stavenhagen et al. |
| 8,524,807 B2 | 9/2013 | Bütikofer |
| 8,524,867 B2 | 9/2013 | Bernett et al. |
| 8,530,067 B2 | 9/2013 | Miyaki et al. |
| 8,652,466 B2 | 2/2014 | Stavenhagen et al. |
| 8,679,492 B2 | 3/2014 | Blein et al. |
| 8,697,071 B2 | 4/2014 | Stavenhagen |
| 8,735,547 B2 | 5/2014 | Lazar et al. |
| 8,753,628 B2 | 6/2014 | Lazar et al. |
| 8,883,992 B2 | 11/2014 | Damschroder et al. |
| 8,946,387 B2 | 2/2015 | Koenig et al. |
| 8,951,517 B2 | 2/2015 | Stavenhagen |
| 8,968,730 B2 | 3/2015 | Koenig et al. |
| 9,028,815 B2 | 5/2015 | Stavenhagen |
| 9,040,041 B2 | 5/2015 | Desjarlais et al. |
| 9,073,993 B2 | 7/2015 | McDonagh et al. |
| 9,096,877 B2 | 8/2015 | Johnson et al. |
| 9,120,856 B2 | 9/2015 | Salles et al. |
| 9,193,798 B2 | 11/2015 | Lazar et al. |
| 9,578,524 B2 | 2/2017 | Amirijoo et al. |
| 9,617,348 B2 | 4/2017 | Desjarlais et al. |
| 9,663,583 B2 | 5/2017 | Vermot-Desroches et al. |
| 9,708,408 B2 | 7/2017 | Stavenhagen et al. |
| 9,714,282 B2 | 7/2017 | Lazar et al. |
| 9,803,020 B2 | 10/2017 | Bernett et al. |
| 9,896,505 B2 | 2/2018 | Damschroder et al. |
| 9,919,061 B2 | 3/2018 | McDonagh et al. |
| 10,113,001 B2 | 10/2018 | Lazar et al. |
| 10,526,408 B2 | 1/2020 | Georgiou et al. |
| 10,617,691 B2 | 4/2020 | Endell et al. |
| 10,626,182 B2 | 4/2020 | Bernett et al. |
| RE49,192 E | 8/2022 | Vermot-Desroches et al. |
| 2004/0136908 A1 | 7/2004 | Olson et al. |
| 2004/0185045 A1 | 9/2004 | Koenig et al. |
| 2005/0123546 A1 | 6/2005 | Umana et al. |
| 2005/0215767 A1 | 9/2005 | Koenig et al. |
| 2005/0260213 A1 | 11/2005 | Koenig et al. |
| 2006/0134709 A1 | 6/2006 | Stavenhagen et al. |
| 2007/0015239 A1 | 1/2007 | Bihoreau et al. |
| 2007/0111281 A1 | 5/2007 | Sondermann et al. |
| 2007/0154473 A1 | 7/2007 | Super et al. |
| 2007/0166306 A1 | 7/2007 | Fey et al. |
| 2008/0138336 A1 | 6/2008 | Damschroder et al. |
| 2008/0206897 A1 | 8/2008 | Yoo et al. |
| 2009/0098124 A1 | 4/2009 | Stavenhagen et al. |
| 2009/0136526 A1 | 5/2009 | McDonagh et al. |
| 2010/0104509 A1 | 4/2010 | King et al. |
| 2010/0196362 A1 | 8/2010 | Stavenhagen et al. |
| 2010/0215651 A1 | 8/2010 | Blein et al. |
| 2010/0255012 A1 | 10/2010 | Schuurman et al. |
| 2010/0272723 A1 | 10/2010 | Bernett et al. |
| 2011/0293609 A1 | 12/2011 | Umana et al. |
| 2011/0294984 A1 | 12/2011 | Umana et al. |
| 2011/0305714 A1 | 12/2011 | Stavenhagen et al. |
| 2011/0312088 A1 | 12/2011 | McDonagh et al. |
| 2012/0082664 A1 | 4/2012 | Bernett et al. |
| 2012/0148576 A1 | 6/2012 | Sharma et al. |
| 2012/0156220 A1 | 6/2012 | Chu et al. |
| 2012/0219551 A1 | 8/2012 | Johnson et al. |
| 2012/0263711 A1 | 10/2012 | Stavenhagen et al. |
| 2012/0269811 A1 | 10/2012 | Johnson et al. |
| 2012/0294853 A1 | 11/2012 | McDonagh et al. |
| 2013/0040831 A1* | 2/2013 | Liu ............ C12Q 1/6886 506/18 |
| 2013/0115657 A1 | 5/2013 | Damschroder et al. |
| 2013/0202606 A1 | 8/2013 | Stavenhagen et al. |
| 2013/0217863 A1 | 8/2013 | Vermot-Desroches |
| 2013/0224190 A1 | 8/2013 | Vermot-Desroches et al. |
| 2013/0330328 A1 | 12/2013 | Herbst et al. |
| 2014/0086906 A1 | 3/2014 | Bernett et al. |
| 2014/0112916 A1 | 4/2014 | Bernett et al. |
| 2014/0199300 A1 | 7/2014 | Besret et al. |
| 2014/0227277 A1 | 8/2014 | Amersdorfer et al. |
| 2014/0286934 A1 | 9/2014 | Blein et al. |
| 2015/0283255 A1 | 10/2015 | McDonagh et al. |
| 2015/0312782 A1 | 10/2015 | Amirijoo et al. |
| 2016/0145335 A1 | 5/2016 | Damschroder et al. |
| 2017/0058030 A1 | 3/2017 | Georgiou et al. |
| 2017/0198040 A1 | 7/2017 | Balke et al. |
| 2018/0000961 A9 | 1/2018 | McDonagh et al. |
| 2018/0009900 A1 | 1/2018 | Bernett et al. |
| 2018/0148511 A9 | 5/2018 | Bernett et al. |
| 2018/0153892 A1 | 6/2018 | Endell et al. |
| 2018/0251572 A1 | 9/2018 | Misaghi et al. |
| 2018/0273621 A1 | 9/2018 | Damschroder et al. |
| 2018/0326087 A1 | 11/2018 | McDonagh et al. |
| 2019/0292269 A1 | 9/2019 | Monnet |
| 2020/0087394 A1 | 3/2020 | Monnet |
| 2020/0206228 A1 | 7/2020 | Endell et al. |
| 2020/0352975 A1 | 11/2020 | Amersdorffer et al. |

FOREIGN PATENT DOCUMENTS

| | | | | |
|---|---|---|---|---|
| EP | 337120 | 10/1989 | | |
| EP | 2175298 | 4/2010 | | |
| EP | 2368911 | 9/2011 | | |
| EP | 2471813 | 7/2012 | | |
| EP | 2708557 | 3/2014 | | |
| WO | WO 1996036360 | 11/1996 | | |
| WO | WO 91/13974 | 9/1997 | | |
| WO | WO 99/51642 | 10/1999 | | |
| WO | WO-2003/011878 | 2/2003 | | |
| WO | WO 2006/0089133 | * | 8/2006 | ........... A61K 39/395 |
| WO | WO2008030564 | 3/2008 | | |
| WO | WO 2012/010562 | * | 1/2012 | ............. C07K 16/28 |
| WO | WO-201229715 | 3/2012 | | |
| WO | WO-2017/032679 | 3/2017 | | |
| WO | WO-2019081983 | 5/2019 | | |

OTHER PUBLICATIONS

Wang, Siao-Yi, et al., "NK-Cell Activation and Antibody-Dependent Cellular Cytotoxicity Induced by Rituximab-Coated Target Cells is Inhibited by the C3b Component of Complement", 2008, 9 pages, vol. 111, Blood.

Vlasveld, L. T., et al., "Treatment of Low-Grade Non-Hodgkin's Lymphoma with Continuous Infusion of Low-Dose Recombinant Interleukin-2 in Combination with the B-Cell-Specific Monoclonal Antibody CLB-CD19", 1995, pp. 37-47, vol. 40, Cancer Immunol Immunother.

Van Der Kolk, L. E., et al., "Complement Activation Plays a Key Role in the Side-Effects of Rituximab Treatment", Jul. 20, 2001, pp. 807-811, vol. 115, British Journal of Haematology.

Treon, S. P., et al., "Tumor Cell Expression of CD59 is Associated with Resistance to CD20 Serotherapy in Patients with B-Cell Malignancies", 2001, pp. 263-271, vol. 24, No. 3, Journal of Immunotherapy.

Shields, R. L., et al., "Lack of Fucose on Human IgG1 N-Linked Oligosaccharide Improves Binding to Human FcγRIII and Antibody-dependent Cellular Toxicity*", Jul. 26, 2002, pp. 26733-26740, vol. 277, No. 30, The Journal of Biological Chemistry.

(56) References Cited

OTHER PUBLICATIONS

Sato, S., et al., "CD10 and CD22 Expression Reciprocally Regulates Tyrosine Phosphorylation of Vav Protein During B Lymphocyte Signaling", Nov. 1997, pp. 13158-13162, vol.

Sarkar, G., et al., "The "Megaprimer" Method of Site-Directed Mutagenesis", 1990, pp. 404-407, vol. 8, No. 4, Research Report, BioTechniques.

Sapra, P., et al., "Internalizing Antibodies are Necessary for Improved Therapeutic Efficacy of Antibody-Targeted Liposomal Drugs", 2002, pp. 7190-7194, vol. 62, Cancer Research.

Sanger, F., et al., "DNA Sequencing with Chain-Terminating Inhibitors (DNA Polymerase/nucleotide Sequences/Bacteriophage øX174)", Dec. 1977, pp. 5463-5467, vol. 74, No. 12, Proc. Natl. Acad. Sci. USA.

Rowland, A. J., et al., "Preclinical Investigation of the Antitumour Effects of Anti-CD19-Idarubicin Immunoconjugates", 1993, pp. 195-202, vol. 37, Cancer Immunol Immunother.

Press, O. W., et al., "Endocytosis and Degradation of Monoclonal Antibodies Targeting Human B-Cell Malignancies", 1989, 8 pages, vol. 49, Cancer Research.

Olejniczak, S. H., et al., "A Quantitative Exploration of Surface Antigen Expression in Common B-Cell Malignancies Using Flow Cytometry", 2006, pp. 93-114, vol. 35, Immunological Investigations.

Nishimura, Y., et al., "Recombinant Human-Mouse Chimeric Monoclonal Antibody Specific for Common Acute Lymphocytic Leukemia Antigen", Feb. 15, 1987, 8 pages, vol. 47, Cancer Research.

Morelle, W., et al., "Analysis of Protein Glycosylation by Mass Spectrometry", 2007, pp. 1585-1602, vol. 2, No. 7, Nature Protocols.

Mølhøj, M., et al., "CD19-/CD3-bispecific Antibody of the BiTE class is far superior to Tandem Diabody with Respect to Redirected Tumor Cell Lysis", 2007, pp. 1935-1943, vol. 44, Molecular Immunology.

Lund, J., et al., "Multiple Interactions of IgG with its Core Oligosaccharide Can Modulate Recognition by Complement and Human Fcγ Receptor I and Influence the Synthesis of its Oligosaccharide Chains[1]", 1996, pp. 4963-4969, vol. 157, The Journal of Immunology.

Lund, J., et al., "A Protein Structural Change in Aglycosylated IgG3 Correlates with Loss of huFcγR1 and huFcγR111 Binding and/or Activation", 1990, pp. 1145-1153, vol. 27, No. 11, Molecular Immunology, Great Britain.

Liu, A. Y., et al., Chimeric Mouse—Human IgG1 Antibody that can Mediate Lysis of Cancer Cells (Immunoglobulin Domain cDNA/DNA Transfection/Tumor Antigen/Complement-Dependent Cytolysis/Antibody-Dependent Cytolysis/Antibody-Dependent Cellular Cytotoxicity), May 1987, pp. 3439-3443, vol. 84, Proc. Natl. Acad. Sci. USA, Medical Sciences.

Lifely, M. R., et al., "Glycosylation and Biological Activity of CAMPATH-1H Expressed in Different Cell Lines and Grown Under Different Culture Conditions", 1995, pp. 813-822, vol. 5, No. 8, Glycobiology.

Li, Yongli, et al., "Rituximab-CD20 Complexes are Shaved from Z138 Mantle Cell Lymphoma Cells in Intravenous and Subcutaneous SCID Mouse Models", 2007, 10 pages, vol. 179, The Journal of Immunology, http://www.jimmunol.org/content/179/6/4263.

Leatherbarrow, R. J., et al., "The Effect of Aglycosylation on the Binding of Mouse IgG to Staphylococcal Protein A", Dec. 1983, pp. 227-230, vol. 164, No. 2, FEBS 0994, Department of Biochemistry, University of Oxford, Oxford, England.

Kyte, J., "A Simple Method for Displaying the Hydropathic Character of a Protein", 1982, pp. 105-132, vol. 157, J. Mol. Biol.

Kumpel, B. M., "Galactosylation of Human IgG Monoclonal Anti-D Produced by EBV-Transformed B-Lymphoblastoid Cell Lines is Dependent of Culture Method and Affects Fc Receptor-Mediated Functional Activity", 1994, pp. 143-151, vol. 5, 3 and 4, Hum. Antibod. Hybridomas.

Kirschfink, Michael, "Targeting Complement in Therapy", 2001, pp. 177-189, vol. 180, Immunological Reviews.

Kabat, E. A., et al., "Identical V Region Amino Acid Sequences and Segments of Sequences in Antibodies of Different Specificities. Relative Contributions of VH and VL Genes, Minigenes, and Complementarity-Determining Regions to Binding of Antibody-Combining Sites", 1991, 12 pages, vol. 147, The Journal of Immunology.

Jenkins, N., et al., "Getting the Glycosylation Right: Implications for the Biotechnology Industry", Aug. 1996, pp. 975-981, vol. 14 Nature Biotechnology.

Hekman, A., et al., "Initial Experience with Treatment of Human B Cell lymphoma with Anti-CD19 Monoclonal Antibody*", 1991, pp. 364-372, vol. 32, Cancer Immunology Immunotherapy.

Hallek, M., et al., "Guidelines for the Diagnosis and Treatment of Chronic Lymphocytic Leukemia: A Report from the International Workshop on Chronic Lymphocytic Leukemia Updating the National Cancer Institute—Working Group 1996 Guidelines", Jun. 15, 2008, vol. 111, No. 12, Blood, The American Society of Hematology.

Ripka, J., et al., "Lectin-Resistant CHO Cells: Selection of Four New Pea Lectin-Resistant Phenotypes", 1986, pp. 51-62, vol. 12, No. 1, Somatic Cell and Molecular Genetics.

Essono, S., et al., "A General Method Allowing the Design of Oligonucleotide Primers to Amplify the Variable Regions form Immunoglobulin cDNA", 2003 pp. 251-266, vol. 279, Journal of Immunological Methods.

Ciucanu, I., et al., "A Simple and Rapid Method for the Permethylation of Carbohydrates", 1984, pp. 209-217, vol. 131, Carbohydrate Research.

Cartron, G., et al., "Therapeutic Activity of Humanized Anti-CD20 Monoclonal Antibody and Polymorphism in IgG Fc γRIII Gene", Feb. 1, 2002, 6 pages, vol. 99, No. 3, Blood, The American Society of Hematology.

Bruenke, J., et al., "Effective Lysis of Lymphoma Cells with a Stabilised Bispecific Single-Chain Fv Antibody Against CD19 and Fc γRIII (CD16)", 2005, pp. 218-228, vol. 130, British Journal of Haematology.

Bienvenu, J., et al., "Tumor Necrosis Factor ⍺ Release is a Major Biological Event Associated with Rituximab Treatment", 2001, pp. 378-384, vol. 2, The Hematology.

Benedict, C. A., et al., "Determination of the Binding Affinity of an Anti-CD34 Single-Chain Antibody Using a Novel, Flow Cytometry Based Assay", 1997, pp. 223-231, vol. 201, Journal of Immunological.

Bargou, R., et al., "Tumor Regression in Cancer Patients by Very Low Doses of a T Cell-Engaging Antibody", 2008, 5 pages, vol. 321, Science American Association for the Advancement of Science.

Bannerji, R., et al., "Apoptotic-Regulatory and Complement-Protecting Protein Expression in Chronic Lymphocytic Leukemia: Relationship to in Vivo Rituximab Resistance", Apr. 5, 2003, pp. 1466-1471, vol. 21, No. 8, Journal of Clinical Oncology.

Boyd, P.N., et al., "The Effect of the Removal of Sialic Acid, Galactose and Total Carbohydrate on the Functional Activity of Campath-1H", 1995, pp. 1311-1318, vol. 32, No. 17/18, Molecular Immunology.

Kabat, "Heavy Constant Chains CB3 Region", pp. 690-723.

Umana, Pablo, et al., "Engineered Glycoforms of an Antineuro-Blastoma IgG1 with Optimized Antibody-Dependent Cellular Cytotoxic Activity", Feb. 1999, pp. 176-180, vol. 17, Nature Biotechnology.

Shinkawa, Toyohide, et al., "The Absence of Fucose but not the Presence of Galactose of Bisecting N-Acetylglucosamine of Human IgG1 Complex-Type Oligosaccharides Shows the Critical Role of Enhancing Antibody-Dependent Cellular Cytotoxicity*" Jan. 31, 2003, pp. 3466-3473, vol. 278. No. 5, The Journal of Biological Chemistry.

Yamane-Ohnuki, Naoko, et al., "Establishment of *FUT8I* Knockout Chinese Hamster Ovary Cells: An Ideal Host Cell Line for Producing Completely Defucosylated Antibodies with Enhanced Antibody-Dependent Cellular Cytotoxicity", Sep. 5, 2004, pp. 614-622, vol. 87, No. 5, Biotechnology and Bioengineering.

Radaev, Sergei, et al., "Recognition of IgG by Fcγ Receptor: The Role of Fc Glycosylation and the Binding of Peptide Inhibitors", May 11, 2001, 7 pages, vol. 276, No. 19, The Journal of Biological Chemistry.

(56) References Cited

OTHER PUBLICATIONS

Niwa, Rinpei, et al., "Enhanced Natural Killer Cell Binding and Activation by Low-Fucose IgG1 Antibody Results in Potent Antibody-Dependent Cellular Cytotoxicity Induction at lower Antigen Density", Mar. 15, 2005, 11 pages, vol. 11, Clinical Cancer Research.
Mori, K., et al., "Engineering Chinese Hamster Ovary Cells to Maximize Effector Function of Produced Antibodies Using FUT8 siRNA", Dec. 30, 2004, pp. 901-908 Vol. 88, No. 7, Biotechnology and Bioengineering.
Lazar, Greg A., et al., "Engineered Antibody Fc Variants with Enhanced Effector Function", Mar. 14, 2006, pp. 4005-4010, vol. 103, No. 11, PNAS, Applied Biological Sciences.
Kumpel, Belinda M., et al., "The Biological Activity of Human Monoclonal IgG anti-D is reduced by β-Galactosidase Treatment", 1995, pp. 82-88, vol. 6 and 3, Hum. Antibod. Hybridomas.
Krapp, S., et al., "Structural Analysis of Human IgG-Fc Glycoforms Reveals a Correlation Between Glycosylation and Structural Integrity", 2003, pp. 979-989, vol. 325, J. Mol. Biol.
Köhler, G., et al., Pillars Article: Continuous Cultures of Fused Cells Secreting Antibody of Predefined Specificity, Aug. 7, 1975, 4 pages, vol. 256, Nature, The Journal of Immunology.
Jefferis, Royston, et al., "A Comparative Study of the N-Linked Oligosaccharide Structures of Human IgG Subclass Proteins", 1990, pp. 529-537, vol. 268, Biochem. J., Great Britain.
Hart, Craig M., et al., "Facilitation of Chromatin Dynamics by SARs", 1998, pp. 519-525, vol. 8, Current Opinion in Genetics & Development.
Liu, A, Y., et al., "Production of a Mouse-Human Chimeric Monoclonal Antibody to CD20 with Potent Fc-Dependent Biologic Activity", Nov. 15, 1987, pp. 3521-3526, vol. 139, No. 10, The Journal of Immunology.
International Search Report for PCT/EP2011/062271 dated Oct. 13, 2011.
Horton Holly M et al: "Potent in vitro and in vivo activity of an Fc-engineered anti-CD19 monoclonal antibody against lymphoma and leukemia", Cancer Research, vol. 68, No. 19, (Oct. 2008), pp. 8049-8057.
Awan Farrukh T et al: "CD19 targeting of chronic lymphocytic leukemia with a novel Fc-domain-engineered monoclonal antibody", Blood, American Society of Hematology, US, vol. 115, No. 6, (Feb. 1, 2010), pp. 1204-1213.
Cardarelli Pina M et al: "A nonfucosylated human antibody to CD19 with potent B-cell depletive activity for therapy of B-cell malignancies", Cancer Immunology, Immunotherapy, Springer, Berlin, DE, vol. 59, No. 2, (Aug. 6, 2009) pp. 257-265.
Stavenhagen Jeffrey B et al: "Fc optimization of therapeutic antibodies enhances their ability to kill tumor cells in vitro and controls tumor expansion in vivo via low-affinity activating fc gamma receptors", Cancer Research, American Association for Cancer Rerearch, US, vol. 67, No. 18, (Sep. 1, 2007), pp. 8882-8890.
Strohl et al: "Optimization of Fc-mediated effector functions of monoclonal antibodies", Current Opinion in Biotechnology, London, GB, vol. 20, No. 6, (Dec. 1, 2009), pp. 685-691.
Masuda et al: "Enhanced binding affinity for FcgammaRIIIa of fucose-negative antibody is sufficient to induce maximal antibody-dependent cellular cytotoxicity", Molecular Immunology, Pergamon, GB, vol. 44, No. 12, (Apr. 17, 2007), pp. 3122-3131.
Moore Gregory L et al: "Engineered Fc variant antibodies with enhanced ability to recruit complement and mediate effector functions", MABS, vol. 2, No. 2, (Mar. 2010), pp. 181-189.
Beers Stephen A et al: "Antigenic modulation limits the efficacy of anti-CD20 antibodies: implications for antibody selection", Blood, American Society of Hematology, US, vol. 115, No. 25, (Jun. 1, 2010) pp. 5191-5201.
Jassal R et al: "Sialylation of human IgG-Fc carbohydrate by transfected rat alpha2,6-sialyltransferase", Biochemical and Biophysical Research Communications, Academic Press Inc. Orlando, FL, US, vol. 286, No. 2, (Aug. 17, 2001), pp. 243-249.
Lund J et al: "Multiple interactions of IgG with its core oligosaccharide can modulate recognition by complement and human Fc gamma receptor I and influence the synthesis of its oligosaccharide chains", Journal of Immunology, American Association of Immunologists, US, vol. 157, No. 11, (Dec. 1, 1996), pp. 4963-4969.
Search Report for International Application No. PCT/EP2018/068672 dated Aug. 3, 2018.
Written Opinion for International Application No. PCT/EP2018/068672 dated, Aug. 3, 2018.
Dony, et al, "Efficiency of CD19 Targeting by Monoclonal Antibodies in Ex Vivo and Mouse Models of Children Acute B-Lymphoblastic Leukemias", pp. 408-409, Jun. 13-16, 2013, vol. 98(s1) Haematologica.
Valentine, et al, "B3.9 Structure and function of the B-cell specific 35-37 kDa CD20 protein", 1987, pp. 440-443, vol. B3.9, B-cell antigens—papers.
Armitage, et al, "Non-Hodgkin lymphoma", Jan. 30, 2017, pp. 1-13, Seminar—http://dx.doi.org/10/1016/S0140-6736(16)32407-2.
Press, et al., "Monoclonal Antibody 1F5 (Anti-CD20) Serotherapy of Human B Cell Lymphomas", Feb. 1987, pp. 584-591, vol. 69, No. 2, Blood \* cited by examiner

VL-R005-2

```
<----------------------------------- L-FR1 - IMGT -----------------------------------
 D   A   V   M   T   Q   T   P   L   S   L   P   V   S   L   G   D   Q   A
GAC GCT GTG ATG ACC CAA ACT CCA CTC TCC CTG CCT GTC AGT CTT GGA GAT CAA GCC
                                               <----- L-CDR1 - IMGT -----
 S   I   S   C   R   S   S   Q   S   L   E   N   S   N   G   N   T   Y   L
TCC ATC TCT TGC AGG TCT AGT CAG AGC CTT GAA AAC AGT AAT GGA AAC ACC TAT TTG
-----> <----------------- L-FR2 - IMGT -----------------
 N   W   Y   L   Q   K   P   G   Q   S   P   Q   L   L   I   Y   R   V   S
AAC TGG TAC CTC CAG AAA CCA GGC CAG TCT CCA CAG CTC CTG ATC TAC AGG GTT TCC
 L-CDR2- IMGT  <----------------- L-FR3 - IMGT -----------------
 N   R   F   S   G   V   L   D   R   F   S   G   S   G   S   G   T   D   F
AAC CGA TTT TCT GGG GTC CTA GAC AGG TTC AGT GGC AGT GGA TCA GGA ACA GAT TTC
-------------------------------------> L-CDR3 - IMGT
 T   L   K   I   S   R   V   E   A   E   D   L   G   V   Y   F   C   L   Q
ACA CTG AAA ATC AGC AGA GTG GAG GCT GAG GAT TTG GGA GTT TAT TTC TGC CTC CAA
------ L-CDR3 - IMGT ------
 V   T   H   V   P   P   T   F   G   A   G   T   K
GTT ACA CAT GTC CCT CCC ACG TTC GGT GCT GGG ACC AAG
```

| A | S | T | K | G | P | S | V | F | P | L | A | P | S | S | K | S | T | S |
|---|---|---|---|---|---|---|---|---|---|---|---|---|---|---|---|---|---|---|
| gcc | tcc | acc | aag | ggc | cca | tcg | gtc | ttc | ccc | ctg | gca | ccc | tcc | aag | agc | acc | tct | |

| G | G | T | A | A | A | L | G | C | L | V | K | D | Y | F | P | E | P | V | T |
|---|---|---|---|---|---|---|---|---|---|---|---|---|---|---|---|---|---|---|---|
| ggg | ggc | aca | gcg | gcc | ctg | ggc | tgc | ctg | gtc | aag | gac | tac | ttc | ccc | gaa | ccg | gtg | acg | |

CH1

| V | S | W | N | S | G | A | L | T | S | G | V | H | T | F | P | A | V | L |
|---|---|---|---|---|---|---|---|---|---|---|---|---|---|---|---|---|---|---|
| gtg | tcg | tgg | aac | tca | ggc | gcc | ctg | acc | agc | ggc | gtg | cac | acc | ttc | ccg | gct | gtc | cta |

| Q | S | S | G | L | Y | S | L | S | S | V | V | T | V | P | S | S | S | L |
|---|---|---|---|---|---|---|---|---|---|---|---|---|---|---|---|---|---|---|
| cag | tcc | tca | gga | ctc | tac | tcc | ctc | agc | agc | gtg | gtc | acc | gtg | ccc | tcc | agc | agc | ttg |

| G | T | Q | T | Y | I | C | N | V | N | H | K | P | S | N | T | K | V | D |
|---|---|---|---|---|---|---|---|---|---|---|---|---|---|---|---|---|---|---|
| ggc | acc | cag | acc | tac | atc | tgc | aac | gtg | aat | cac | aag | ccc | agc | aac | acc | aag | gtg | gac |

Hinge

| K | K | V | E | P | K | S | C | D | K | T | H | T | C | P | P | C | P | A |
|---|---|---|---|---|---|---|---|---|---|---|---|---|---|---|---|---|---|---|
| aag | aaa | gtt | gag | ccc | aaa | tct | tgt | gac | aaa | act | cac | aca | tgc | cca | ccg | tgc | cca | gca |

| P | E | L | L | G | G | P | S | V | F | L | F | P | P | K | P | K | D | T |
|---|---|---|---|---|---|---|---|---|---|---|---|---|---|---|---|---|---|---|
| cct | gaa | ctc | ctg | ggg | gga | ccg | tca | gtc | ttc | ctc | ttc | cca | cca | aaa | ccc | aag | gac | acc |

| L | M | I | S | R | T | P | E | V | T | C | V | V | V | D | V | S | H | E |
|---|---|---|---|---|---|---|---|---|---|---|---|---|---|---|---|---|---|---|
| ctc | atg | atc | tcc | cgg | acc | cct | gag | gtc | aca | tgc | gtg | gtg | gtg | gac | gtg | agc | cac | gaa |

```
D    P    E    V    K    F    N    W    Y    V    D    G    V    E    V    H    N    A    K
gac  cct  gag  gtc  aag  ttc  aac  tgg  tac  gtg  gac  ggc  gtg  gag  gtg  cat  aat  gcc  aag CH2
T    K    P    R    E    E    Q    Y    N    S    T    Y    R    V    V    S    V    L    T
aca  aag  ccg  cgg  gag  gag  cag  tac  aac  agc  acg  tac  cgt  gtg  gtc  agc  gtc  ctc  acc V    L    H    Q    D    W    L    N    G    K    E    Y    K    C    K    V    S    N    A
gtc  ctg  cac  cag  gac  tgg  ctg  aat  ggc  aag  gag  tac  aag  tgc  aag  gtc  tcc  aac  gca A    L    P    A    P    I    A    K    T    I    S    K    A    K    G    Q    P    R    E
gcc  ctc  cca  gcc  ccc  atc  gcg  aaa  acc  atc  tcc  aaa  gcc  aaa  ggg  cag  ccc  cga  gaa P    Q    V    Y    T    L    P    P    S    R    D    E    L    T    K    N    Q    V    S
cca  cag  gtg  tac  acc  ctg  ccc  cca  tcc  cgg  gat  gag  ctg  acc  aag  aac  cag  gtc  agc CH3
L    T    C    L    V    K    G    F    Y    P    S    D    I    A    V    E    W    E    S
ctg  acc  tgc  ctg  gtc  aaa  ggc  ttc  tat  ccc  agc  gac  atc  gcc  gtg  gag  tgg  gag  agc N    G    Q    P    E    N    N    Y    K    T    T    P    L    V    L    D    S    D    G
aat  ggg  cag  ccg  gag  aac  aac  tac  aag  acc  acg  cct  ctc  gtg  ctg  gac  tcc  gac  ggc S    F    F    L    Y    S    K    L    T    V    D    K    S    R    W    Q    Q    G    N
tcc  ttc  ttc  ctc  tac  agc  aag  ctc  acc  gtg  gac  aag  agc  agg  tgg  cag  cag  ggg  aac
```

```
V   F   S   C   S   V   M   H   E   A   L   H   N   H   Y   T   Q   K   S
gtc ttc tca tgc tcc gtg atg cat gag gct ctg cac aac cac tac acg cag aag agc L   S   L   S   P   G   K   *
ctc tcc ctg tct ccg ggt aaa tga
```

```
A    S    T    K    G    P    S    V    F    P    L    A    P    S    S    K    S    T    S
gcc  tcc  acc  aag  ggc  cca  tcg  gtc  ttc  ccc  ctg  gca  ccc  tcc  tcc  aag  agc  acc  tct G    G    T    A    A    A    L    G    C    L    V    K    D    Y    F    P    E    P    V    T
ggg  ggc  aca  gcg  gcc  ctg  ggc  tgc  ctg  gtc  aag  gac  tac  ttc  ccc  gaa  ccg  gtg  acg
```

CH1

```
V    S    W    N    S    G    A    L    T    S    G    V    H    T    F    P    A    V    L
gtg  tcg  tgg  aac  tca  ggc  gcc  ctg  acc  agc  ggc  gtg  cac  acc  ttc  ccg  gct  gtc  cta Q    S    S    G    L    Y    S    L    S    S    V    V    T    V    P    S    S    S    L
cag  tcc  tca  gga  ctc  tac  tcc  ctc  agc  agc  gtg  gtc  acc  gtg  ccc  tcc  agc  agc  ttg G    T    Q    T    Y    I    C    N    V    N    H    K    P    S    N    T    K    V    D
ggc  acc  cag  acc  tac  atc  tgc  aac  gtg  aat  cac  aag  ccc  agc  aac  acc  aag  gtg  gac
```

Hinge

```
K    K    V    E    P    K    S    C    D    K    T    H    T    C    P    P    C    P    A
aag  aaa  gtt  gag  ccc  aaa  tct  tgt  gac  aaa  act  cac  aca  tgc  cca  ccg  tgc  cca  gca P    E    L    L    G    G    P    S    V    F    L    F    P    P    K    P    K    D    T
cct  gaa  ctc  ctg  ggg  gga  ccg  tca  gtc  ttc  ctc  ttc  ccc  cca  aaa  ccc  aag  gac  acc L    M    I    S    R    T    P    E    V    T    C    V    V    V    D    V    S    H    E
ctc  atg  atc  tcc  cgg  acc  cct  gag  gtc  aca  tgc  gtg  gtg  gtg  gac  gtg  agc  cac  gaa
```

FIG. 2D

```
  D   P   E   V   K   F   N   W   Y   V   D   G   V   E   V   H   N   A   K
  gac cct gag gtc aag ttc aac tgg tac gtg gac ggc gtg gag gtg cat aat gcc aag
                          CH2

T   K   P   R   E   E   Q   Y   N   S   T   L   R   V   V   S   V   L   T
  aca aag ccg cgg gag gag cag tac aac agc acg ctc cgt gtg gtc agc gtc ctc acc V   L   H   Q   D   W   L   N   G   K   E   Y   K   C   K   V   S   N   A
  gtc ctg cac cag gac tgg ctg aat ggc aag gag tac aag tgc aag gtc tcc aac gca A   L   P   A   P   I   E   K   T   I   S   K   A   K   G   Q   P   R   E
  gcc ctc cca gcc ccc atc gag aaa acc atc tcc aaa gcc aaa ggg cag ccc cga gaa P   Q   V   Y   T   L   P   P   S   R   D   E   L   T   K   N   Q   V   S
  cca cag gtg tac acc ctg ccc cca tcc cgg gat gag ctg acc aag aac cag gtc agc
                                          CH3

L   T   C   L   V   K   G   F   Y   P   S   D   I   A   V   E   W   E   S
  ctg acc tgc ctg gtc aaa ggc ttc tat ccc agc gac atc gcc gtg gag tgg gag agc N   G   Q   P   E   N   N   Y   K   T   T   P   L   V   L   D   S   D   G
  aat ggg cag ccg gag aac aac tac aag acc acg cct ctc gtg ctg gac tcc gac ggc S   F   F   L   Y   S   K   L   T   V   D   K   S   R   W   Q   Q   G   N
  tcc ttc ttc ctc tac agc aag ctc acc gtg gac aag agc agg tgg cag cag ggg aac
```

FIG. 2E

```
V   F   S   C   S   V   M   H   E   A   L   H   N   H   Y   T   Q   K   S
gtc ttc tca tgc tcc gtg atg cat gag gct ctg cac aac cac tac acg cag aag agc L   S   L   S   P   G   K   *
ctc tcc ctg tct ccg ggt aaa tga
```

Figure 3 (end)
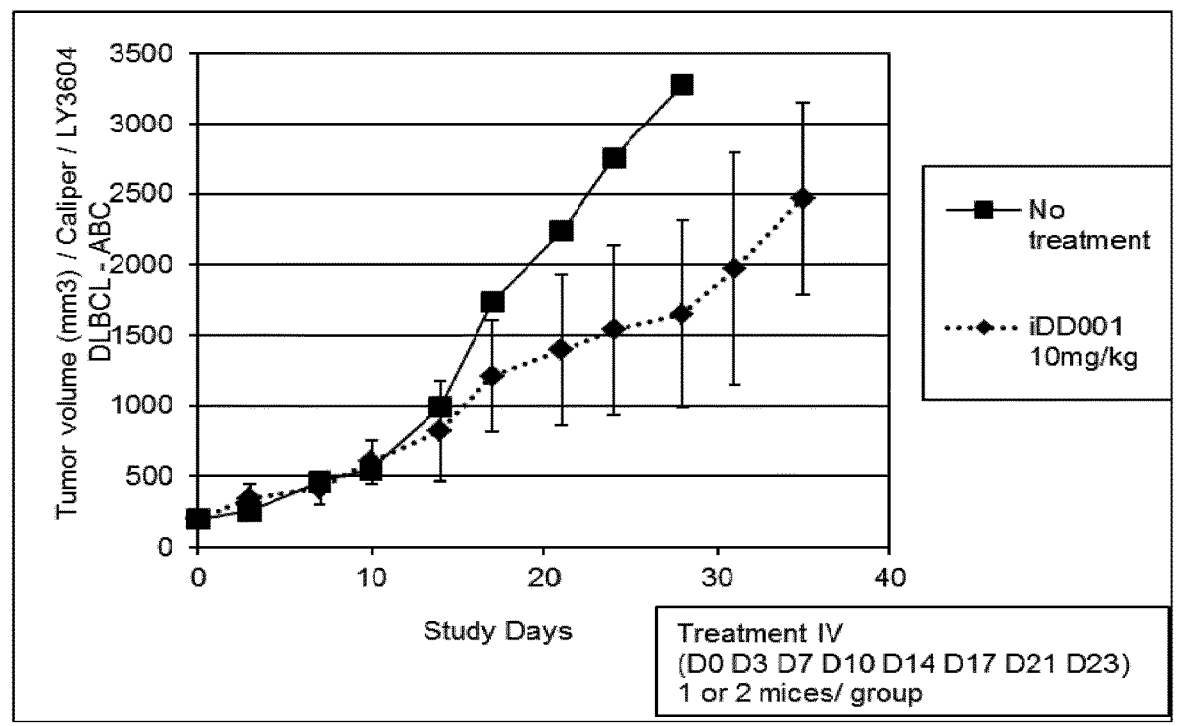
C
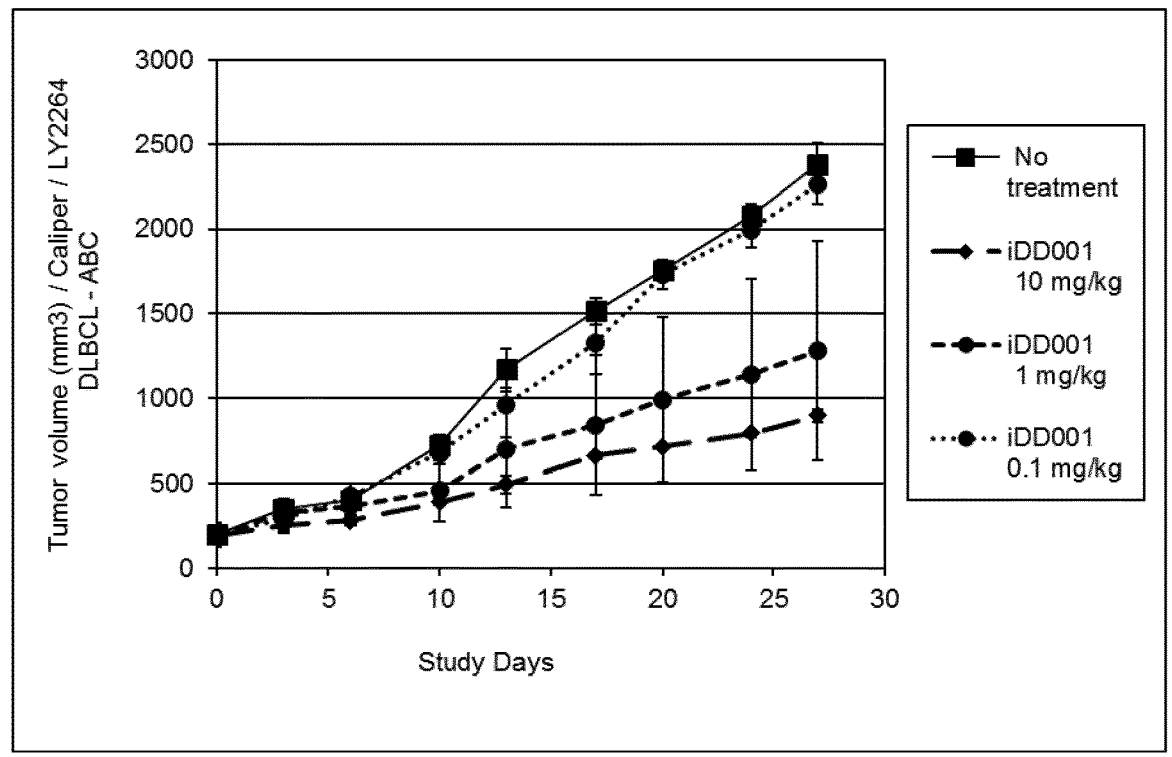
D

A

B

Figure 4 (end)
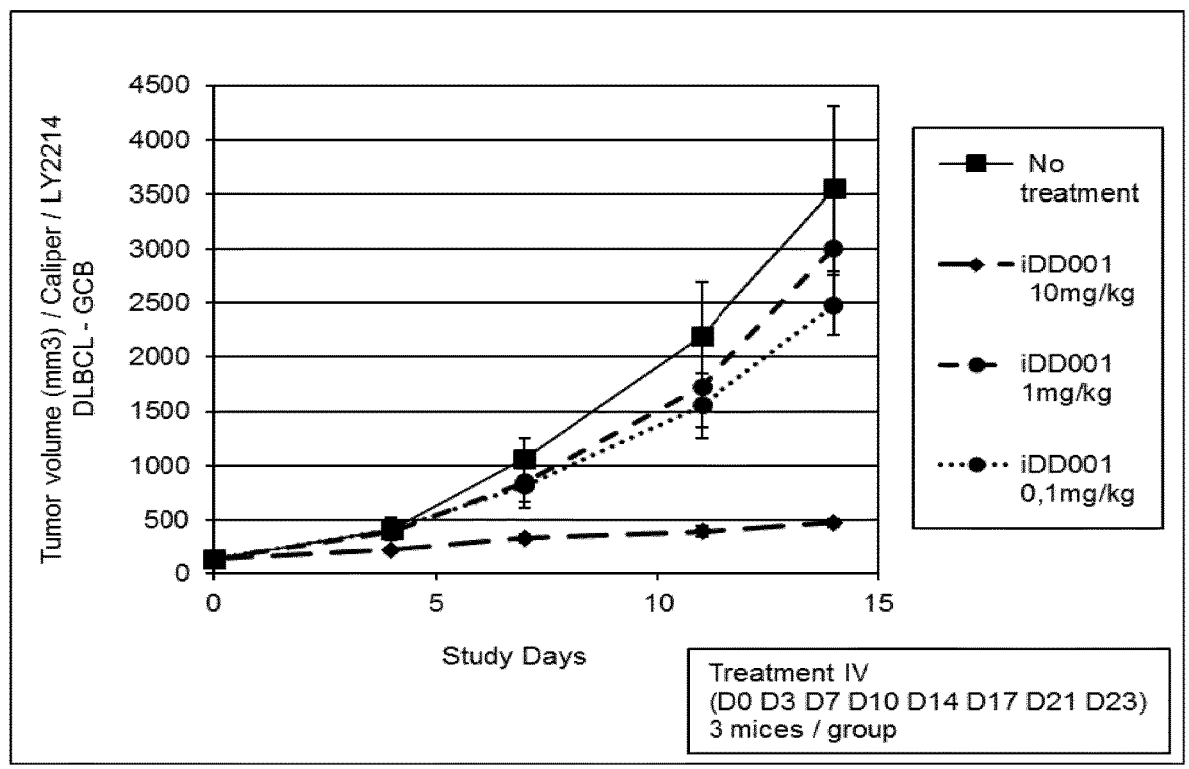
C

A

B

Figure 5 (end)
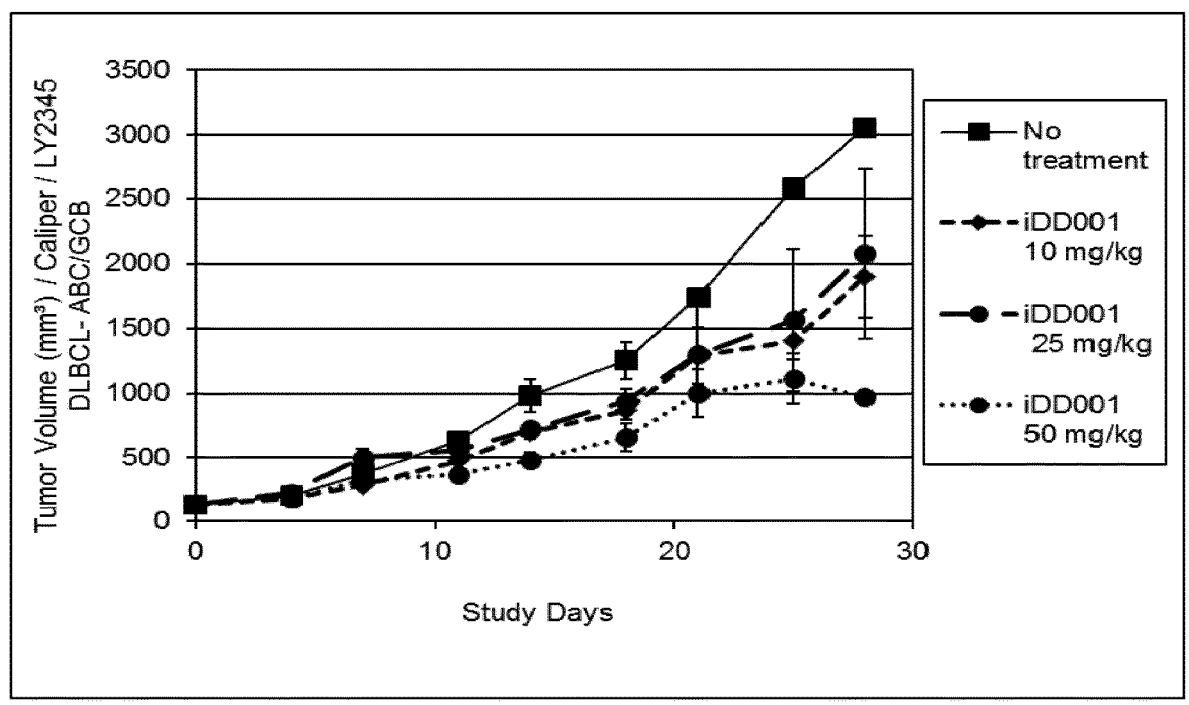
C

```
                <----------------------------- L-FR1 - IMGT ----------------------------
  D   I   Q   M   T   Q   S   P   A   S   L   S   A   S   V   G   G   R   V   T   I   T   C
 GAC ATA CAA ATG ACA CAA TCT CCC GCT AGC CTT AGT GCA TCA GTT GGC GGC CGA GTT ACC ATC ACA TGC

---------->  ____ L-CDR1 - IMGT ____<-------------------- L-FR2 - IMGT --------------------
  K   A   S   Q   S   I   N   N   W   L   A   W   Y   Q   H   K   P   G   K   A   P   K   L
 AAA GCT AGC CAA AGC ATC AAC AAC TGG CTG GCT TGG TAT CAG CAC AAG CCC GGT AAG GCA CCT AAG CTG

---------->__L-CDR2 __<-------------------------- L-FR3 - IMGT --------------------
  L   I   S   G   A   S   T   L   E   S   G   V   P   S   R   F   S   G   S   G   S   G   K
 CTC ATC TCT GGG GCA TCT ACT CTG GAG AGT GGT GTC CCA TCC CGA TTT TCC GGC TCT GGA AGC GGA AAG

----------------------------------------------------------------------------------->
  D   Y   T   L   T   I   S   S   L   Q   P   E   D   V   A   T   Y   Y   C   Q   Q   S   W
 GAC TAT ACA CTG ACC ATC AGC AGT TTG CAA CCT GAA GAC GTT GCC ACT TAT TAC TGC CAA CAG TCC TGG

_ L-CDR3 - IMGT_____
  N   T   P   W   T   F   G   Q   G   T   K   V   E   I   K   R   T   V   A   A   P   S   V
 AAT ACA CCC TGG ACC TTC GGC CAA GGG ACC AAG GTG GAG ATC AAG CGA ACT GTG GCT GCA CCA TCT GTC

F   I   F   P   P   S   D   E   Q   L   K   S   G   T   A   S   V   V   C   L   L   N   N
 TTC ATC TTC CCG CCA TCT GAT GAG CAG TTG AAA TCT GGA ACT GCC TCT GTT GTG TGC CTG CTG AAT AAC

F   Y   P   R   E   A   K   V   Q   W   K   V   D   N   A   L   Q   S   G   N   S   Q   E
 TTC TAT CCC AGA GAG GCC AAA GTA CAG TGG AAG GTG GAT AAC GCC CTC CAA TCG GGT AAC TCC CAG GAG

S   V   T   E   Q   D   S   K   D   S   T   Y   S   L   S   S   T   L   T   L   S   K   A
 AGT GTC ACA GAG CAG GAC AGC AAG GAC AGC ACC TAC AGC CTC AGC AGC ACC CTG ACG CTG AGC AAA GCA

D   Y   E   K   H   K   V   Y   A   C   E   V   T   H   Q   G   L   S   S   P   V   T   K
 GAC TAC GAG AAA CAC AAA GTC TAC GCC TGC GAA GTC ACC CAT CAG GGC CTG AGC TCG CCC GTC ACA AAG

S   F   N   R   G   E   C
 AGC TTC AAC AGG GGA GAG TGT
```

TREATMENT OF B CELL MALIGNANCIES USING AFUCOSYLATED PRO-APOPTOTIC ANTI-CD19 ANTIBODIES IN COMBINATION WITH ANTI CD20 ANTIBODIES OR CHEMOTHERAPEUTICS

FIELD OF THE INVENTION

The present invention relates to the field of combination therapies using antibodies or antibodies and chemotherapeutic agents. In particular, the invention relates to the use of a preferably afucosylated pro-apotic anti-CD19 antibody in the treatment of CD19 positive B-cell malignancy, and more particularly Diffuse Large B Cell Lymphoma (DLBCL) and Follicular Lymphoma (FL) expressing CD19, preferably in a combination therapy with another antibody and/or a chemotherapeutic agent.

BACKGROUND OF THE INVENTION

Surgery, chemotherapy, hormonal therapy and/or radiotherapy are the general therapeutic approaches to fight cancer. In the last decades, the use of biological therapy or immunotherapy has also been adopted. Still, many tumors respond only partially to the existing therapies and cases of resistance also occur. Therefore, there is a strong need for alternative cancer treatments.

The B-cell types of Non-Hodgkin's lymphoma (NHL) include small lymphocytic/B-cell chronic leukemia (SLL/B-CLL), lymphomplasmacytoid lymphoma (LPL), mantle cell lymphoma (MCL), follicular lymphoma (FL), diffuse large cell lymphoma (DLBCL) and Burkitt's lymphoma (BL) (Armitage et al, 2017, pii: S0140-6736(16)32407-2).

Follicular lymphoma (FL) is the second most common type of non-Hodkin lymphoma (NHL) and accounts for 10%-20% of all lymphomas. FL typically affects individuals 55-60 years of age. FL is characterized by painless swelling in several lymph node sites, with bone marrow involvement in approximately 70% of cases. Rituximab as a single agent or in combination with first-line chemotherapy is the standard of care for FL. Although FL is frequently responsive to treatment, therapy is very rarely, if ever, curative.

In other attempts to improve the prognosis, MAb have also been tested in combination with other molecules. For example, an anti-CD19 MAb has been assessed for its synergistic activity when combined with a purine analog (Fludarabine), a bruton's tyrosine kinase inhibitor (Ibrutinib) or a phosphoinositide 3-kinase inhibitor (Idelalisib) for the treatment of non-Hodgkin's lymphoma (WO 2013024095, WO 201 61 8901 4 and WO 2017032679 respectively).

The treatment of DLBCL with anti-CD19 maytansinoid immunoconjugate (SAR3419) combined with rituximab was investigated in a disseminating model of DLBCL (patent family WO 2013017540). No statistical significance was obtained for the survival improvement observed following treatment with SAR3419 and rituximab over the single treatment subjects.

In another study (patent family WO2012067981), efficacy of an afucosylated anti-CD19 MAb (16C4-afuc MAb), alone or in combination with an anti CD20 antibody, was investigated. 164-afuc Ab was demonstrated to induce the death of CD19-expressing cells via ADCC (antibody-dependent cell cytotoxicity) but not CDC (complement-dependent cytotoxicity). The combinatory treatment with anti 16C4-afuc MAb and anti CD20 MAb to treat B cell lymphoma was investigated. The longer duration of the antitumor activity conferred by the combinatory treatment over either single treatment was pronounced in some but not all Burkitt models, while it was more modest in the presented models of other B-cell tumors (DLBCL and ALL). Also, experimental results do not demonstrate that the combinatory treatment with MAb anti-CD19 and anti-CD20 was capable of inducing the complete remission from the tumor.

Therefore, the identification of an anti-CD19 MAb 19 that could function well in combination with an anti-CD20 Mab, for a combinatory treatment capable of inducing tumor regression and remission in patients suffering of B-cell related tumors, would be helpful.

Based on the analysis of gene expression profiling, two main subtypes of Diffuse Large B cell lymphoma (DLBCL) can be identified: the germinal centre B-cell-like (GCB) and the activated B-cell-like (ABC) subtypes. GCB-DLBCL correlates with an increased expression of CD10, BCL6 and other markers of germinal centre differentiation. The prognosis of GCB-DLBLC is better than that of ABC-DLBCL, but 30% of GCB-DLBCL cannot be treated with the mainstays of therapy, the R-CHOP regimen (combination therapy with rituximab, cyclophosphamide, doxorubicin, vincristine, prednisone). ABC DLBCL is characterised by the constitutive activation of the NF-kB signalling pathway. Several clinical trials suggest an improved prognosis in ABC DLBCL patients when the R-CHOP treatment is combined either with bortezomib (proteasome inhibitor, which prevents NF-kB activation) or lenalidomide (inducer of IFN-β production), (Khan Net al, 2015, Blood 126(16):1869-70).

There is still a strong need of a combinatory treatment capable of inducing tumour regression and/or remission in patients suffering of B-cell related tumours such as FL and DLBCL.

SUMMARY OF THE INVENTION

The present invention relates to an anti-CD19 antibody for use in treating non-Hodgkin's lymphoma expressing CD19 and possibly CD20, more particularly Diffuse Large B Cell Lymphoma (DLBCL) expressing CD19 or Follicular Lymphoma (FL) expressing CD19, in a patient in need thereof.

In an embodiment, the antibody comprises the CDRs of the murine antibodies R005-1 or R005-2 whose VH and VL amino acid sequences are depicted on the following table:

|        | Amino acid sequence VH | Amino acid sequence VL |
| --- | --- | --- |
| R005-1 | SEQ ID NO: 29 | SEQ ID NO: 31 |
| R005-2 | SEQ ID NO: 33 | SEQ ID NO: 35 |

In an embodiment, the antibody comprises the CDRs of the humanized antibody IDD001 (results from humanization of R005-1) whose VH and VL amino acid sequences are depicted on the following table. More precisely, the VL sequence per se is amino acids 1-103 on SEQ ID NO: 37, and the VH sequence per se is amino acids 1-121 on SEQ ID NO: 39.

|        | Amino acid sequence Heavy Chain | Amino acid sequence Light Chain |
| --- | --- | --- |
| IDD001 | SEQ ID NO: 39 | SEQ ID NO: 37 |

In an embodiment, the antibody comprises a variant human IgG1 Fc region.

This variant region comprises an amino acid substitution at each of the amino acid positions 243, 292, 300, 305, 396, or 243, 292, 300, 305, 326, 396 or 243, 292, 300, 305, 326, 333, 396 of the human IgG1 Fc region. These amino acid residues in the Fc region are numbered according to the numbering system of Kabat. This anti-CD19 antibody is for use in treating DLBCL or FL. DLBCL and FL concerned by the present invention are those whose cells express CD19.

In an embodiment, the antibody is afucosylated.

In an embodiment, the antibody is pro-apoptotic.

In an embodiment, the antibody comprises the above-mentionned CDRs and one of the above-mentionned variant human IgG1 Fc regions. Preferably the VH and VL sequences are humanized, with human frame-work regions and possibly CDR changes. This antibody may be afucosylated.

In a preferred embodiment, these antibodies comprise the CDRs of the antibody R005-1 whose VH and VL amino acid sequences are SEQ ID NO: 29, respectively SEQ ID NO: 31.

In a preferred embodiment, the VH and VL sequences are humanized, in particular they comprise the above mentioned CDRs and human frame-work regions or humanized frame-work regions. In a still preferred embodiment, some of the CDRs may also be humanized, especially as disclosed herein after for the CDR1 and CDR2 of the VL sequence. In a typical embodiment having humanized frame-work regions and VL CDR1 and CDR2, the antibody comprises the VH and VL sequences presented on SEQ ID NO: 39 (aas 1-123) and 37 (aas 1-103). In a preferred embodiment the antibody is IDD001 whose sequence of the whole Heavy chain and of the whole Light chain is on FIG. 10 and on sequences SEQ ID NO: 39, respectively 37.

The present invention also relates to a pharmaceutical comprising an anti-CD19 antibody according to the present invention and a suitable pharmaceutical carrier, for its use in treating non-Hodgkin's lymphoma expressing CD19 and possibly CD20, in particular for its use in treating DLBCL or FL expressing CD19 and possibly CD20.

In an embodiment, this anti-CD19 antibody is for use in treating DLBCL, subtype ABC, GCB and/or ABC/GCB. More particularly, this antibody is for use in combination therapy with another agent such as a chemotherapeutic drug. Say chemotherapeutic drug may be a vinca alkaloid, in particular vincristine.

In another embodiment, this anti-CD19 antibody is for use in treating FL. More particularly, this antibody is for use in combination therapy with another agent such as a monoclonal antibody. Say monoclonal antibody may be an anti-CD20 antibody, in particular rituxan.

The present invention also relates to a kit or pharmaceutical composition comprising a first composition comprising an anti-CD19 antibody according to the present invention and a suitable pharmaceutical carrier and a second composition comprising another antibody or chemotherapeutic drug as disclosed herein and a suitable pharmaceutical carrier, in particular for its use in in treating non-Hodgkin's lymphoma expressing CD19 and possibly CD20, in particular for its use in treating DLBCL or FL expressing CD19 and possibly CD20, wherein the first and the second composition are for simultaneous, separate or sequential administration to a patient in need thereof.

Another object of the invention is a humanized monoclonal anti-CD19 antibody, having the CDRs of the IDD001 antibody as disclosed herein, and more particularly having the VH sequence 1-121 on SEQ ID NO: 39 and the VL sequence 1-103 on SEQ ID NO: 37. In an embodiment, this humanized antibody comprises a variant human IgG1 Fc region, wherein this variant region preferably comprises an amino acid substitution at each of the amino acid positions 243, 292, 300, 305, 396, or 243, 292, 300, 305, 326, 396 or 243, 292, 300, 305, 326, 333, 396 of the human IgG1 Fc region, wherein the numbering of the amino acid residues in the Fc region is the one of Kabat. Several embodiments will be presented hereinafter. In an embodiment, the humanized monoclonal anti-CD19 antibody has a Heavy Chain of SEQ ID NO: 39 and a Light Chain of SEQ ID NO: 37. These humanized antibodies are for use in treating cancer, especially cancers expressing CD19.

The present invention also relates to a method for treating non-Hodgkin's lymphoma expressing CD19 and possibly CD20, in particular for treating DLBCL or FL expressing CD19 and possibly CD20, wherein a pharmaceutical composition or a kit as disclosed herein is administered in sufficient amount to the patient.

The invention relates to a method for treating Diffuse Large B Cell Lymphoma (DLBCL) in a patient in need thereof, comprising administering an efficient amount of a pharmaceutical composition according to the invention, or a humanized anti-CD19 monoclonal antibody as disclosed herein.

The invention also relates to a method for treating Follicular Lymphoma (FL), comprising administering an efficient amount of a pharmaceutical composition according to the invention, and an efficient amount of an anti-CD20 monoclonal antibody.

The invention even further relates to a method for treating Follicular Lymphoma (FL) in a patient in need thereof, comprising administering an efficient amount of a humanized anti-CD19 monoclonal antibody as disclosed herein.

The invention also concerns a method for treating a cancer in a patient in need thereof, comprising administering an efficient amount of an humanized monoclonal anti-CD19 antibody, having the CDRs of the IDD001 antibody as disclosed herein, and more particularly having the VH sequence 1-121 on SEQ ID NO: 39 and the VL sequence 1-103 on SEQ ID NO: 37. In an embodiment, this humanized antibody comprises a variant human IgG1 Fc region, wherein this variant region preferably comprises an amino acid substitution at each of the amino acid positions 243, 292, 300, 305, 396, or 243, 292, 300, 305, 326, 396 or 243, 292, 300, 305, 326, 333, 396 of the human IgG1 Fc region, wherein the numbering of the amino acid residues in the Fc region is the one of Kabat. Several embodiments will be presented hereinafter. In an embodiment, the humanized monoclonal anti-CD19 antibody has a Heavy Chain of SEQ ID NO: 39 and a Light Chain of SEQ ID NO: 37. In particular the cancer is expressing CD19.

DETAILED DESCRIPTION OF THE INVENTION

Anti-CD19 antibody

CD19 is a type I transmembrane glycoprotein of 95 kDA, expressed in B cells and in follicular dendritic cells and not expressed in stem cells, in pre-B cells and in normal myeloid cells. CD19 expression in B cells commences in the pre-B cell stage and is preserved throughout their differentiation into plasma cells. As part of the B cell receptor (BCR), CD19 participates to the regulation of B cell activation and to the induction of a humoral immunity. Importantly, CD19 is expressed in the vast majority of cases of B-cell related tumors and the expression is preserved throughout the tumor development. Anti-CD19 monoclonal antibodies having modified human IgG1 Fc have been disclosed in WO2012/1999. This disclosure further provides chimeric, humanized and human anti-CD19 antibodies, anti-CD19 antibody fusion proteins, and fragments thereof.

More particularly, the invention relates to an anti-CD19 antibody comprising (i) the CDRs of one of the antibodies R005-1, R005-2 or IDD001 whose VH and VL amino acid sequences are depicted on the following table,

|  | Amino acid sequence VH | Amino acid sequence VL |
| --- | --- | --- |
| R005-1 | SEQ ID NO: 29 | SEQ ID NO: 31 |
| R005-2 | SEQ ID NO: 33 | SEQ ID NO: 35 |
| IDD001 | 1-121 SEQ ID NO: 39 | 1-103 SEQ ID NO: 37 |

(2i) a variant human IgG1 Fc region, wherein this variant region comprises an amino acid substitution at each of the amino acid positions 243, 292, 300, 305, 396, or 243, 292, 300, 305, 326, 396 or 243, 292, 300, 305, 326, 333, 396 of the human IgG1 Fc region, wherein the numbering of the amino acid residues in the Fc region is the one of Kabat, for use in treating Diffuse Large B Cell Lymphoma (DLBCL) or Follicular Lymphoma (FL), whose cells are expressing CD19.

In an embodiment, the Fc region is modified at each of the amino acid positions Phe243, Arg292, Tyr300, Val305, Lys326 and Pro396 (Kabat) of the human IgG1 Fc region.

According to the invention, in the modified IgG1 Fc region, Phe243 is substituted by Leu, Trp, Tyr, Arg, Ile, Ala or Gin; Arg292 is substituted by Pro, Ala, or Gly; Tyr300 is substituted by Leu, Lys, Phe, Ala or Ile; Val305 is substituted by Leu, Ala or Ile; Lys326 is substituted by Ala, Val, Glu, Asp, Met, Ser, Asn or Trp; Pro396 is substituted by Leu, Ala or Ile.

According to the invention, this Fc region has the amino acid sequence depicted on SEQ ID NO: 1 (Fc34). A nucleic acid coding for this Fc region is depicted on SEQ ID NO: 2.

In another embodiment, the Fc region is modified at each of the amino acid positions Phe243, Arg292, Tyr300, Val305, Lys326, Glu333 and Pro396 (Kabat) of the human IgG1 Fc region.

According to the invention, in the modified Fc IgG1 Fc region, Phe243 is substituted by Leu, Trp, Tyr, Arg, Ile, Ala or Gin; Arg292 is substituted by Pro, Ala, or Gly; Tyr300 is substituted by Leu, Lys, Phe, Ala or Ile; Val305 is substituted by Leu, Ala or Ile; Lys326 is substituted by Ala, Val, Glu, Asp, Met, Ser, Asn or Trp; Pro396 is substituted by Leu, Ala or Ile, and Glu333 is substituted by Val, Gly, Ala, Gin, Asp, Asn, Lys, Arg or Ser.

According to this invention, this Fc region has the amino acid sequence depicted on SEQ ID NO: 3 (Fc24). A nucleic acid coding for this Fc region is depicted on SEQ ID NO: 4. A variant is the herein-called Fc39 region, having one difference with respect to Fc24, say Val305 is substituted by Ile.

In an embodiment, the antibody comprises the VH and VL amino acid sequences are depicted on the following table:

|  | Amino acid sequence VH | Amino acid sequence VL |
| --- | --- | --- |
| mR005-1 | SEQ ID NO: 29 | SEQ ID NO: 31 |
| mR005-2 | SEQ ID NO: 33 | SEQ ID NO: 35 |
| IDD001 | 1-121 on SEQ ID NO: 39 | 1-103 on SEQ ID NO: 37 |

In a preferred embodiment, the antibody comprises the CDRs of the antibody mR005-1 whose VH and VL amino acid sequences are SEQ ID NO: 29, respectively SEQ ID NO: 31, or it comprises the VH and VL amino acid sequences of SEQ ID NO: 29, respectively SEQ ID NO: 31. This antibody may comprise) a variant human IgG1 Fc region, wherein this variant region comprises an amino acid substitution at each of the amino acid positions 243, 292, 300, 305, 396, or 243, 292, 300, 305, 326, 396 or 243, 292, 300, 305, 326, 333, 396 of the human IgG1 Fc region, as disclosed herein. Said antibody may be afucosylated.

In a preferred embodiment, the VH and VL sequences are humanized, in particular they comprise the above mentioned CDRs and human frame-work regions or humanized framework regions. In a typical embodiment, the antibody comprises the VH and VL sequences presented on FIG. 10 and SEQ ID NO: 39 (VH) and 37 (VL).

The CDRs of the anti-CD19 antibody R005-1 of the invention are:

|  | SEQ ID NO: | Sequence IMGT | SEQ ID NO: | Sequence Kabat | SEQ ID NO: | Sequence (Common numbering system) |
| --- | --- | --- | --- | --- | --- | --- |
|  |  |  | VHmR005-1 |  |  |  |
| CDR1 | 5 | GYAFSSYW | 11 | SYWVN | 16 | SSYW |
| CDR2 | 6 | IYPGDGDT | 12 | QIYPGDGDTNYNGKFKG | 6 | IYPGDGDT |
| CDR3 | 7 | ARSITTVVGCAMDY | 13 | SITTVVGCAMDY | 13 | SITTVVGCAMDY |
|  |  |  | VLmR005-1 |  |  |  |
| CDR1 | 8 | DHINNW | 14 | KASDHINNWLA | 8 | DHINNW |
| CDR2 | 9 | GAT | 15 | GATTLET | 9 | GAT |
| CDR3 | 10 | QQSWNTPWT | 10 | QQSWNTPWT | 10 | QQSWNTPWT |

The CDRs of the anti-CD19 antibody R005-2 of the invention are:

| | SEQ ID NO: | Sequence IMGT | SEQ ID NO: | Sequence Kabat | SEQ ID NO: | Sequence (Common numbering system) |
|---|---|---|---|---|---|---|
| | | | | VHmR005-2 | | |
| CDR1 | 17 | GYTFTSYV | 23 | SYVMH | 28 | TSYV |
| CDR2 | 18 | VNPYNDGT | 24 | YVNPYNDGTKYNEKFKG | 18 | VNPYNDGT |
| CDR3 | 19 | ARGPYYYGSSPFDY | 25 | GPYYYGSSPFDY | 25 | GPYYYGSSPFDY |
| | | | | VLmR005-2 | | |
| CDR1 | 20 | QSLENSNGNTY | 26 | RSSQSLENSNGNTYLN | 20 | QSLENSNGNTY |
| CDR2 | 21 | RVS | 27 | RVSNRFS | 21 | RVS |
| CDR3 | 22 | LQVTHVPPT | 22 | LQVTHVPPT | 22 | LQVTHVPPT |

The CDRs of the anti-CD19 humanized antibody IDD001 of the invention are the same as those of R005-1, except for CDR1 and CDR2 of the VL chain:

| | SEQ ID NO: | Sequence IMGT | SEQ ID NO: | Sequence Kabat | SEQ ID NO: | Sequence (Common numbering system) |
|---|---|---|---|---|---|---|
| | | | | VH IDD001 | | |
| CDR1 | 5 | GYAFSSYW | 11 | SYWVN | 16 | SSYW |
| CDR2 | 6 | IYPGDGDT | 12 | QIYPGDGDTNYNGKFKG | 6 | IYPGDGDT |
| CDR3 | 7 | ARSITTVVGCAMDY | 13 | SITTVVGCAMDY | 13 | SITTVVGCAMDY |
| | | | | VL IDD001 | | |
| CDR1 | 41 | QSINNW | 42 | KASQSINNWLA | 41 | QSINNW |
| CDR2 | 43 | GAS | 44 | GASTLET | 43 | GAS |
| CDR3 | 10 | QQSWNTPWT | 10 | QQSWNTPWT | 10 | QQSWNTPWT |

By definition, these CDRs include variant CDRs, by deletion, substitution or addition of one or more amino acid(s), which variant keeps the specificity of the original CDR. The common numbering system provides for a CDR definition having the shortest amino acid sequences or the minimal CDR definition.

In an embodiment, the antibody comprises the CDRs whose sequence is depicted on SEQ ID NO: 16, 6, 13 and/or 8, 9, 10. In an embodiment, the antibody comprises the CDRs whose sequence is depicted on SEQ ID NO: 5, 6, 7 and/or 8, 9, 10. In an embodiment, the antibody comprises the CDRs whose sequence is depicted on SEQ ID NO: 11, 12, 13 and/or 14, 15, 10. In an embodiment, the antibody comprises the CDRs whose sequence is depicted on SEQ ID NO: 28, 18, 25 and/or 20, 21, 22. In an embodiment, the antibody comprises the CDRs whose sequence is depicted on SEQ ID NO: 17, 18, 19 and/or 20, 21, 22. In an embodiment, the antibody comprises the CDRs whose sequence is depicted on SEQ ID NO: 23, 24, 25 and/or 26, 27, 22. In an embodiment, the antibody comprises the CDRs whose sequence is depicted on SEQ ID NO: 17, 18, 19 and/or 20, 21, 22. In an embodiment, the antibody comprises the CDRs whose sequence is depicted on SEQ ID NO: 23, 24, 25 and/or 26, 27, 22.

In an embodiment, the antibody comprises the CDRs whose sequence is depicted on SEQ ID NO: 5, 6, 7 and/or 41, 43, 10. In an embodiment, the antibody comprises the CDRs whose sequence is depicted on SEQ ID NO: 11, 12, 13 and/or 42, 44, 10. In an embodiment, the antibody comprises the CDRs whose sequence is depicted on SEQ ID NO: 16, 6, 13 and/or 41, 43, 10.

According to a feature, the anti-CD19 antibodies the invention have been produced in mammal cells, which, along the mutated region of the invention, leads to a non-fucosylated or afucosylated antibody according to the invention. The mammal cell may be a wild-type cell. It may be a rodent cell, in particular a CHO cell. The rodent cell may be wild-type, such as in particular a wild-type CHO. The antibodies have a glycosylation profile resulting from their production in that cell. Wild-type is used in its usual meaning, say is relates to the phenotype of the typical form of a species as it occurs in nature.

In particular, from the transfected cells, e.g. wild-type CHO, the invention allows to express recombinant antibodies carrying a common N-linked oligosaccharide structure of a biantennary-type that comprises long chains with terminal GlcNac that are galactosylated and non-fucosylated. According to a preferred feature, the monoclonal antibody has a low level of fucose, as described in WO2012/010562.

In an embodiment, the anti-CD19 antibody is able to generate ADCC and no CDC. As an example of antibody having this profile is one having a variant human IgG1 Fc region comprising an amino acid substitution at each of the amino acid positions 243, 292, 300, 305, 396. Such antibody was described in U.S. Pat. No. 9,120,856, incorporated herein by reference.

In another embodiment, the anti-CD19 antibody is able to generate CDC and ADCC activity. Aq examples of antibodies having this profile is one having a variant human IgG1 Fc region comprising an amino acid substitution at each of the amino acid positions 243, 292, 300, 305, 326, 396 or 243, 292, 300, 305, 326, 333, 396. Such antiboidies ared disclosed in WO 2012/010562.

In an embodiment, these antibodies having the variable regions as disclosed herein trigger programmed cell death or apoptosis.

In an embodiment, these antibodies comprise one Fab comprising the CDRs, or the VH and VL regions of R005-1, R005-2 or IDD001, and the like, and one Fab specific to another tumor antigen, especially an antigen on cancer B cell, as disclosed infra, e.g. CD20.

Antl-CD20 Antibodies

The combination therapy described herein may further comprise anti-CD20 antibodies.

Any suitable anti-CD20 antibody may be used in accordance with the methods and compositions described herein. Suitable anti-CD20 antibodies include, for example, known anti-CD20 antibodies, commercially available anti-CD20 antibodies, or anti-CD20 antibodies developed using methods well known in the art Examples of antibodies which bind the CD20 antigen include: "C2B8" which is now called "Rituximab" ("RITUXAN™"); the yttrium-[90]-labeled 2B8 murine antibody designated "Y2B8" or "Ibritumomab Tiuxetan" (ZEVALIN™) (U.S. Pat No. 5,736,137, expressly incorporated herein by reference); murine IgG2a "BI," also called "Tositumomab," (Beckman Coulter) optionally labeled with 1311 to generate the "1311-B1" antibody (iodine 1131 tositumomab, BEXXAR™) (U.S. Pat No. 5,595,721, expressly incorporated herein by reference); murine monoclonal antibody "1F5" (Press et al. Blood 69(2):584-591 (1987) and variants thereof including "framework patched" or humanized 1F5 (WO03/002607, Leung, S.); ATCC deposit HB-96450; murine 2H7 and chimeric 2H7 antibody (U.S. Pat No. 5,677,180, expressly incorporated herein by reference); humanized 2H7; huMax-CD20 (Genmab, Denmark); AME-133 (Applied Molecular Evolution); A20 antibody or variants thereof such as chimeric or humanized A20 antibody (cA20, hA20, respectively) (US 2003/0219433, Immunomedics); and monoclonal antibodies L27, G28-2, 93-1B3, B-Cl or NU-B2 available from the International Leukocyte Typing Workshop (Valentine et al., In: Leukocyte Typing HI (McMichael, Ed., p.440, Oxford University Press (1987)). In an exemplary embodiment the methods and compositions of the disclosure utilize rituximab, or an antigen binding fragment thereof, in combination with an anti-CD19 antibody, or fragment thereof.

The complete nucleic acid and amino acid sequences for the light chain variable region and the heavy chain variable region or rituximab are disclosed in U.S. Pat. No. 5,736,137. In particular, the nucleic acid and amino acid sequences for the light chain variable region of rituximab are disclosed in FIG. 4 and SEQ ID NO: 6 of U.S. Pat. No. 5,736,137. The nucleic acid and amino acid sequence for the heavy chain variable region of rituximab are disclosed in FIG. 5 and SEQ ID NO: 9 of U.S. Pat. No. 5,736,137. The nucleic acid and amino acid sequences of SEQ ID NOs: 6 and 9 and FIGS. 4 and 5 of U.S. Pat. No. 5,736,137 are expressly incorporated herein by reference. Rituximab may also be made by a CHO cell transfectoma comprising the vector DNA present in the E. coli host cell deposited with the American Type Culture Collection (ATCC) under accession number.69119. Rituximab may also be produced from hybridoma 2B8, which is deposited with the ATCC under accession number HB 11388.

A CD20 antibody may be also a monoclonal human, humanized or chimeric anti-CD20 antibody. Anti-CD20 antibodies used in compositions and methods of the disclosure can be naked antibodies, immunoconjugates or fusion proteins. In certain embodiments, an anti-CD20 antibody of the disclosure may mediate human antibody-dependent cellular cytotoxicity (ADCC), complement-dependent cell-mediated cytotoxicity (CDC), and/or apoptosis in an amount sufficient to deplete circulating B cells. In exemplary embodiments, an anti-CD20 antibody of the disclosure is an anti-CD20 antibody that has been engineered to have enhanced ADCC activity relative to the parent antibody. Methods for creating antibody variants having enhanced ADCC activity are described above. In certain embodiments, an anti-CD20 antibody of the disclosure is an afucosylated antibody having enhanced ADCC activity.

Chemotherapeutic agents

Other examples of agents employed for cancer therapy are agents for targeted therapy. These agents interfere with tumor growth by impairing specific molecular mechanisms that participate to tumor initiation and/or progression. Agents for targeted therapy are small molecules or antibodies and are commonly classified according to the molecular target. Examples of molecular targets of targeted therapy are proteins participating to cell signalling, apoptosis, gene transcription, DNA repair, cell cycle progression and/or checkpoint, angiogenesis, invasion and metastasis.

Targeting CD19 with the antibodies of the present invention in combination with existing chemotherapeutic treatments will be more effective in killing the tumor cells than chemotherapy alone. A wide variety of drugs have been employed in chemotherapy of cancer.

Chemotherapeutic agents can be classified in groups according to their mode of action. A non-exhausitve list of chemotherapy classes follows hereafter: alkylating agents (e.g cyclophosphamide), anthracyclines (e.g. doxorubicin), cytoskeletal disruptors (e.g. paclitaxel), epothilones (e.g. ibxabepilone), histone deacetylase inhibitors (e.g. vorinostat), inhibitors of topoisomerase (e.g. irinotecan), kinase inhibitors (e.g. imatinib), nucleotide analogs and precursor analogs (e.g. azacytidine), peptide antibiotics (e.g. bleomycin), platinum-based agents (e.g. cisplatin), retinoids (e.g. tretinoin), vinca alkaloids and derivatives (e.g. vincristine).

Other agents used for cancer therapy, commonly classified as agents for hormonal therapy, include hormones, inhibitors of hormone synthesis, hormone receptor antagonists.

In one approach, antibody treatment or regimen, including combination of at least two antibodies, is added to a standard chemotherapy regimen, in treating a cancer patient. In an embodiment, the additional monoclonal antibody is directed against an antigen of cancerous B cell or lymphocyte, such as CD20.

For those combinations in which the antibody and additional anti-cancer agent(s) exert a synergistic effect against cancer cells, the dosage of the additional agent(s) may be reduced, compared to the standard dosage of the second agent when administered alone. The antibody may be co-administered with an amount of an anti-cancer drug that is effective in enhancing sensitivity of cancer cells.

In one method of the invention, targeting CD19 and CD20 with antibody combination or bispecific antibody, is administered to the patient prior to administration of a chemotherapeutic agent. One alternative method comprises administering the chemotherapeutic agent prior to administering the antibody combination or the bispecific antibody and chemotherapeutic agent on an alternative schedule. In another embodiment, the antibody combination or bispecific antibody and chemotherapeutic agent are administered simultaneously.

Thus the present invention encompasses the use of a bispecific or multivalent monoclonal antibody directed to CD19 and another antigen expressed by cancer B cells, especially CD20. This antibody comprises a Fab specific to CD19 and a Fab specific to the other target. Especially, the Fab specific to CD19 comprises VH and VL regions as disclosed herein, defined by the CDRs or the whole VH and VL regions of R005-1, R005-2 or, preferably, IDD001. In case the bispecific antibody also targets CD20, it is possible to use in addition to the Fab specific to CD19 as disclosed herein, a Fab from any anti-CD20 monoclonal antibody disclosed supra, e.g. from Rituxan. Preferably, the bispecific antibody comprises a human IgG1 Fc, especially a Fc mutated as disclosed herein, such as Fc24, Fc34 or Fc39. Such a bispecific antibody is also encompassed by the present invention on the monoclonal antibodies and is also an object of the invention.

The method of the invention may provide for the inclusion in a therapeutic regimen involving the use of at least one other treatment method, such as irradiation, chemotherapy with small molecule or antibody. The method of the invention may directly include the administration of a sufficient amount of at least one additional antibody directed against another target and/or at least one chemotherapeutic drug (such as small molecule), for a simultaneous, separate or sequential administration with antibody(ies) of the invention, to a mammal, including man. This combination more generally is useful for cancers (in particular aggressive cancers) which do not respond well to treatment with the drug alone or the antibodies/antibody of the invention alone, and for which the combination leads to a synergistic effect.

Modifications and Changes to Antibodies

Modifications and changes may be made in the structure of a polypeptide of the present invention and still obtain a molecule having like characteristics. In other words, these modifications and changes are within the skill of the skilled person. For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like properties.

Based on its general knowledge on the amino acids, the person skilled in the art is able, including by trial-and-assay routine experimentation, to determine amino acids and positions that may be deleted, added or substituted without significantly changing the functionality of the Fc region or of any other part of the antibody, including the binding domain.

The Phe243 substitution by Leu, Trp, Tyr, Arg, Ile, Ala or Gln; Arg292 substitution by Pro, Ala, or Gly; Tyr300 substitution by Leu, Lys, Phe, Ala or Ile; Val305 substitution by Leu, Ala or Ile; Lys326 substitution by Ala, Val, Glu, Asp, Met, Ser, Asn or Trp; Pro396 substitution by Leu, Ala or Ile, and Glu333 substitution by Val, Gly, Ala, Gln, Asp, Asn, Lys, Arg, Ala or Ser, have all been assayed one by one in a chR005-1 Fc24 monoclonal antibody and proved to be acceptable substitutions to provide for ADCC whole blood and CDC in human serum.

The antibodies of the invention may be a monoclonal antibody, a chimeric antibody, a humanized antibody, a full human antibody, a bispecific antibody (e.g. against CD19 and CD20), an association MAb, multivalent antibody composition, an antibody drug conjugate or an antibody fragment with one or two specities at least. A "humanized antibody" or "chimeric humanized antibody" shall mean an antibody derived from a non human antibody, typically a murine antibody, that retains or substantially retains the antigen-binding properties of the parental antibody, but which is less immunogenic in humans.

Methods for producing the antibodies are known from the skilled person.

For producing the anti-CD19 antibody of the invention, the mammal cells, preferably rodent cells such as CHO cells, preferably wild-type cells (e.g. wild-type CHO cells) may be transfected with one or several expression vectors. Preferably, the cells may be co-transfected with an expression vector for light chain and with an expression vector for heavy chain. For the production of antibodies useful in the invention, the person skilled in the art may refer to WO2012/010562, which is incorporated herein by reference.

Combination Therapy

As used herein the term "combination" is used in its broadest sense and means that a subject is treated with at least two therapeutic regimens. As used herein, the term "drugs" may encompass antibody and chemotherapeutic agent.

Thus, "combination antibody therapy" for treating FL is intended to mean a subject is treated with at least two drug regimens, more particularly, with at least one anti-CD20 antibody in combination with at least one anti-CD19 antibody, but the timing of administration of the different antibody regimens can be varied so long as the beneficial effects of the combination of these antibodies is achieved. Treatment with an anti-CD20 antibody in combination with an anti-CD19 antibody can be at the same time (e.g. simultaneously or concurrently), or at different times (e.g. consecutively or sequentially), or a combination thereof.

Also, "combination therapy" for treating DLBCL is intended to mean a subject is treated with at least two drug regimens, more particularly, with at least one chemotherapeutic agent, e.g. vincristine, in combination with at least one anti-CD19 antibody, but the timing of administration of the different regimens can be varied so long as the beneficial effects of the combination of these drugs is achieved. Treatment with a chemotherapeutic agent, e.g.

vincristine, in combination with an anti-CD19 antibody can be at the same time (e.g. simultaneously or concurrently), or at different times (e.g. consecutively or sequentially), or a combination thereof.

For the purposes of the present disclosure, administering at the same time (e.g., simultaneously) refers to administering the drugs together in same formulation or in separate formulations wherein the administration may be a few minutes to a few hours apart, but no more than one day. As used herein administering at different times (e.g., sequentially) refers to administering the drugs of the combination therapy a few hours to days, weeks and even months apart.

Therefore, in certain embodiments a subject undergoing combination therapy can receive both drugs at the same time (e.g., simultaneously) or at different times (e.g., sequentially, in either order, on the same day, or on different days), so long as the therapeutic effect of the combination of both drugs is caused in the subject undergoing therapy. In some embodiments, the combination of drugs will be given simultaneously for one dosing, but other dosings will include sequential administration, in either order, on the same day, or on different days. Where the two drugs are administered simultaneously, they can be administered as separate pharmaceutical compositions, each comprising either drug of the combination, or can be administered as a single pharmaceutical composition comprising both of these drugs.

Therapeutic Activity

Tumor response can also be assessed for changes in tumor morphology (e.g., overall tumor burden, tumor size, and the like) or disappearance of tumor using the usual techniques at the disposal of the clinicians and laboratories, such as screening techniques such as magnetic resonance imaging (MBS) scan, x-radiographic imaging, computed tomographic (CT) scan, flow cytometry or fluorescence-activated cell sorter (FACS) analysis, bioluminescent imaging, for example, luciferase imaging, bone scan imaging, and tumor biopsy sampling including bond marrow aspiration (BMA). The methods of the disclosure comprise using combination therapy which confers a positive therapeutic response to a subject in need of a treatment for B cell diseases such as FL and DLBCL. A positive therapeutic response with respect to the combination treatment using an anti-CD20 antibody and an anti-CD19 antibody (e.g. to treat FL) or using an anti-CD19 antibody and a chemotherapeutic agent, such as vincristine (e.g. to treat DLBCL) is intended to mean an improvement in the disease in association with the anti-tumor activity of these drugs, and/or an improvement in the symptoms associated with the disease. That is, an antiproliferative effect, the prevention of further tumor outgrowths, a reduction in tumor size, a reduction in the number of cancer cells, and/or a decrease in one or more symptoms mediated by neoplastic B cells can be observed. Thus, for example, an improvement in the disease may be characterized as a complete response.

Combination therapy will preferably induce a regression or a remission of non-Hogkin's lymphoma expressing CD19, in particular of FL or DLCBL expressing CD19. Combination therapy may also induce therapeutic effect, including cell death or apoptosis, on non-Hogkin's lymphoma expressing CD19 that are resistant to current treatments with antibodies and/or chemotherapy, such as some DLBCLs, e.g. of the ABC subtype.

The term "Regression" means a reduction in the size of the tumor mass; a reduction in metastatic invasiveness of the tumor; a reduction in the rate of tumor growth; an increased patient survival rate; and/or an increase in observed clinical correlates of improved prognosis such as increased tumor infiltrating lymphocytes and decreased tumor vascularization; and the like. Regression may be regarded as a "partial response", say at least about a 50% decrease in all measurable tumor burden (e.g., the number of tumor cells present in the subject) in the absence of new lesions and persisting for at least one month.

The term "Remission" means that the tumor or the tumor cells are no longer detectable. Remission may be regarded as a "complete response", say an absence of clinically detectable disease with normalization of any previously abnormal radiographic studies, bone marrow, and cerebrospinal fluid (CSF). Such a response must persist for at least one month following treatment according to the methods of the disclosure.

A combination of the invention can be used as a "therapeutic composition" to inhibit growth of mammalian, particulary human, cancer cells as a combination therapy, and/or in further combination with radiation therapy. An effective amount of a therapeutic composition is administered preferably to inhibit or reverse progression of cancers that are expressing CD19, or otherwise result in a statistically significant increase in remission, or progression-free survival (i.e., the length of time during and after treatment in which a patient is living with said targeted cancer, i.e. DLBCL or FL, that does not get worse), or overall survival (also called "survival rate"; i.e., the percentage of people in a study or treatment group who are alive for a certain period of time after they were diagnosed with or treated for cancer) relative to treatment with a control.

Pharmaceutical Compositions

The drugs used in the present combination therapy are administered at a therapeutically effective dose. The term "therapeutically effective dose," "therapeutically effective amount," or "effective amount" is intended to be an amount of the anti-CD19 antibody that, when administered in combination with an amount of the anti-CD20 antibody (e.g. in treating FL) or the chemotherapeutic agent (e.g. in treating DLBCL), brings about a positive therapeutic response with respect to treatment of a subject for a cancer comprising neoplastic B cells, such as FL and DLBCL. In some embodiments, a therapeutically effective dose of either each drug is in the range from about 0.1 mg/kg to about 200 mg/kg, for example from about 1 mg/kg to up to about 100 mg/kg. In some embodiments, the dosage can be 1, 3, 5, 10, 15, 20, 25, or 30 mg/kg. The inventions provides combination therapy or regimen with at least two different antibodies or at least one antibody and ant least one chemotherapeutic agent. By result of this, the therapeutic effective dose of one drug (antibody or chemotherapeutic agent) required for a given therapeutic effect may be lower than if used alone, so the low dosage values (e.g. equal or less than 60 mg/kg) given may be sufficient amount, e.g. 1, 3, 5, 10, 15, 20, 25, or 30 mg/kg.

Such "therapeutically effective dose," "therapeutically effective amount," or "effective amount" can be routinely determined by those of skilled in the art. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, etc. It will also be appreciated by those of stalled in the art that the dosage may be dependent on the stability of the administered peptide.

The pharmaceutical compositions can be administered by injection, that is, intravenously, intramuscularly, intracutaneously, subcutaneously, intraduodenally or intraperitoneally. Other pharmaceutical delivery systems can also be employed, for example, liposomes.

An anti-CD19 monoclonal antibody of the present invention can be administered prior to and/or subsequent to (collectively, "sequential treatment"), and/or simultaneously with ("concurrent treatment") a specific second monoclonal antibody or a chemotherapeutic agent according to the present invention. Sequential treatment (such as pretreatment, post-treatment, or overlapping treatment) of the combination, also includes regimens in which the drugs are alternated, or wherein one component is administered long-term and the other(s) are administered intermittently. Components of the combination may be administered in the same or in separate compositions, and by the same or different routes of administration.

A pharmaceutical composition comprising a therapeutic composition of the present invention may contain formulation materials for modifying, maintaining or preserving, for example, the pH, osmolarity, viscosity, clarity, color, isotonicity, odor, sterility, stability, rate of dissolution or release, adsorption, or penetration of the composition. The primary vehicle or carrier in a pharmaceutical composition may be either aqueous or non-aqueous in nature. For example, a suitable vehicle or carrier may be water for injection or physiological saline, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute therefore. In one embodiment of the present invention, binding agent compositions may be prepared for storage by mixing the selected composition having the desired degree of purity with optional formulation agents (Remington's Pharmaceutical Sciences, supra) in the form of a lyophilized cake or an aqueous solution. Further, the binding agent product may be formulated as a lyophilizate using appropriate excipients such as sucrose.

The formulation components are present in concentrations that are acceptable to the site of administration. For example, buffers are used to maintain the composition at physiological pH or at slightly lower pH, typically within a pH range of from about 5 to about 8. A particularly suitable vehicle for parenteral administration is sterile distilled water in which a binding agent is formulated as a sterile, isotonic solution, properly preserved. Yet another preparation can involve the formulation of the desired molecule with an long-lasting agent that provide for the controlled or sustained release of the product which may then be delivered via a depot injection (such as injectable microspheres, bio-erodible particles, polymeric compounds (polylactic acid, polyglycolic acid), beads, or liposomes).

In another aspect, pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances that increase the viscosity of the suspension, such as sodium carboxymethyl cellulose, sorbitol, or dextran. Additional pharmaceutical compositions will be evident to those skilled in the art, including formulations involving binding agent molecules in sustained- or controlled-delivery formulations.

Techniques for formulating a variety of other sustained- or controlled-delivery means, such as liposome carriers, bio-erodible microparticles or porous beads and depot injections, are also known to those skilled in the art. The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

For any compound, the therapeutically effective dose can be estimated initially either in cell culture assays or in animal models such as mice, rats, rabbits, dogs, pigs, or monkeys. An animal model may also be used to determine the appropriate concentration range and route of administration. Such information can then be used to determine useful doses and routes for administration in humans. The exact dosage will be determined in light of factors related to the subject requiring treatment. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation. The frequency of dosing will depend upon the pharmacokinetic parameters of the molecule in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

BRIEF DESCRIPTION OF THE DRAWINGS

FIGS. 1A-1D: The nucleotide and amino acids sequences of the murine MAbs R005-1 and R005-2 MAbs, (A): $V_H$ (B): VL. Amino acids are shown as one-letter codes.

|  | Amino acid sequence VH | Nucleic acid sequence VH | Amino acid sequence VL | Nucleic acid sequence VL |
| --- | --- | --- | --- | --- |
| mR005-1 | SEQ ID NO: 29 | SEQ ID NO: 30 | SEQ ID NO: 31 | SEQ ID NO: 32 |
| mR005-2 | SEQ ID NO: 33 | SEQ ID NO: 34 | SEQ ID NO: 35 | SEQ ID NO: 36 |

FIGS. 2A-2F: The amino acids and nucleic acid sequences of chimeric Fc24 (SEQ ID NO: 3 and 4) or Fc34 (SEQ ID NO: 1 and 2) variant MAb. The sequences of Fc39 is the same as sequence of Fc24, with an Ile at position 305. Amino acids are shown as one-letter codes.

According to the literature, the amino acid numbering of Fc region is based to the Kabat data base, (CH1: aa n° 118 to 215; Hinge: aa n° 216 to 230; CH2: aa n° 231 to 340; CH3: aa n° 341 to 447). Variations between the various Fc used in the invention with respect to native Fc (Fc0):

| Name of the mutant | Mutations with respect to native human IgG1 Fc (Fc0) |
| --- | --- |
| Fc34 | F243L/R292P/Y300L/V305L/K326A/P396L |
| Fc24 | F243L/R292P/Y300L/V305L/K326A/E333A/P396L |
| Fc39 | F243L/R292P/Y300L/V305I/K326A/E333A/P396L |

Figure 3:
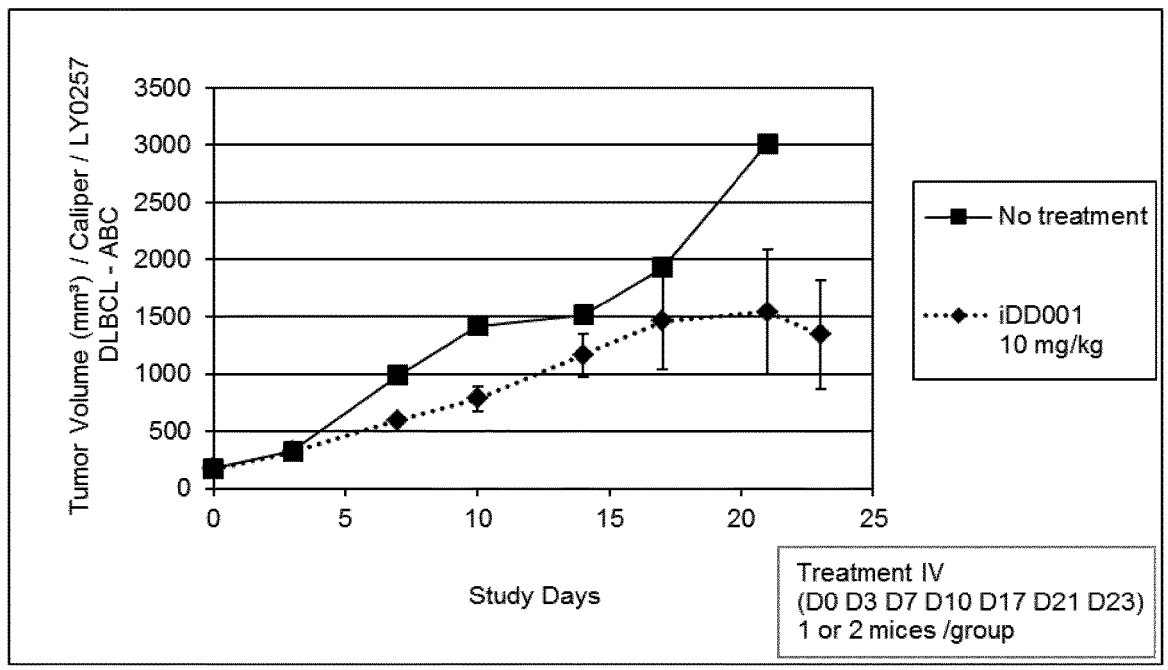
Figure 3:
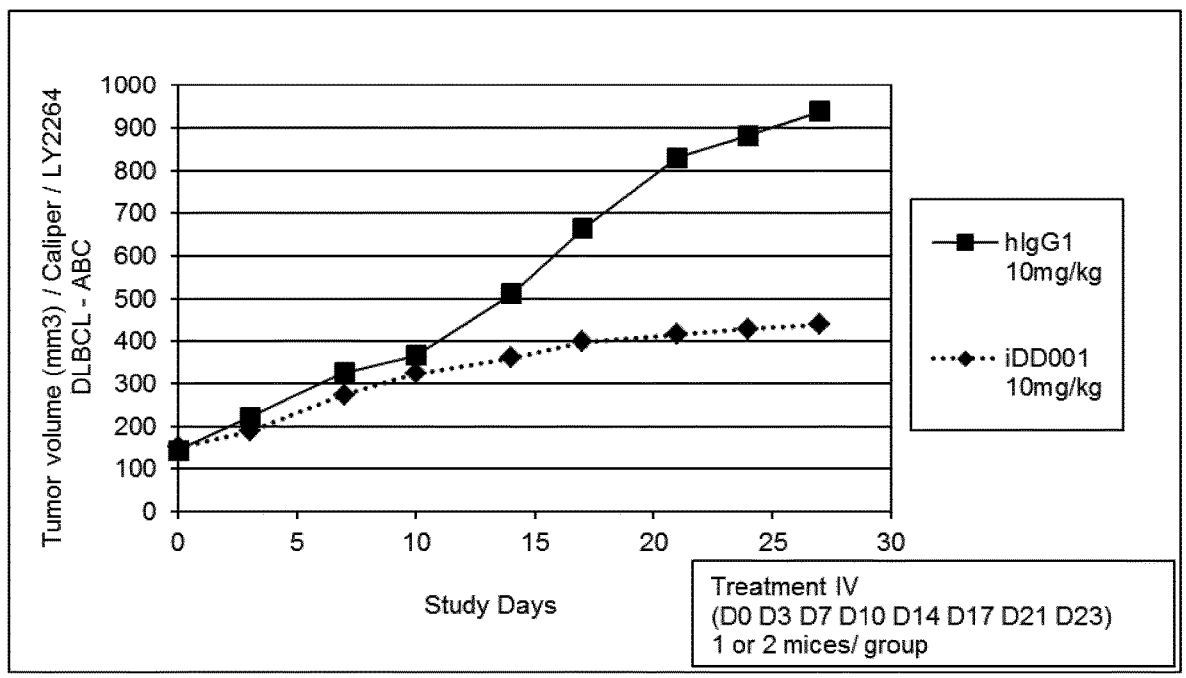

FIG. 3: In vivo inhibition of tumour growth of DLBCL subtype ABC with MAb anti-CD19/IDD001. 3A: xenograft model LY0257; 3B: xenograft model LY2264; 3C: xenograft model LY3604; 3D: xenograft model LY2264 with dose variations.

Figure 4:
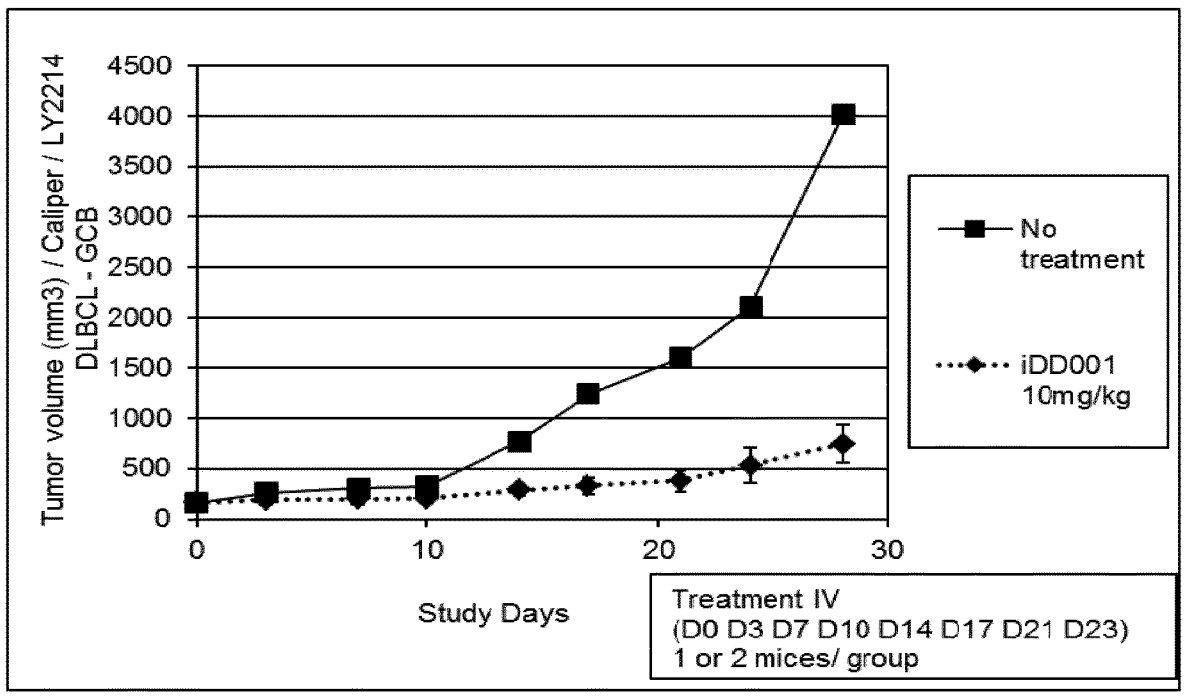
Figure 4:
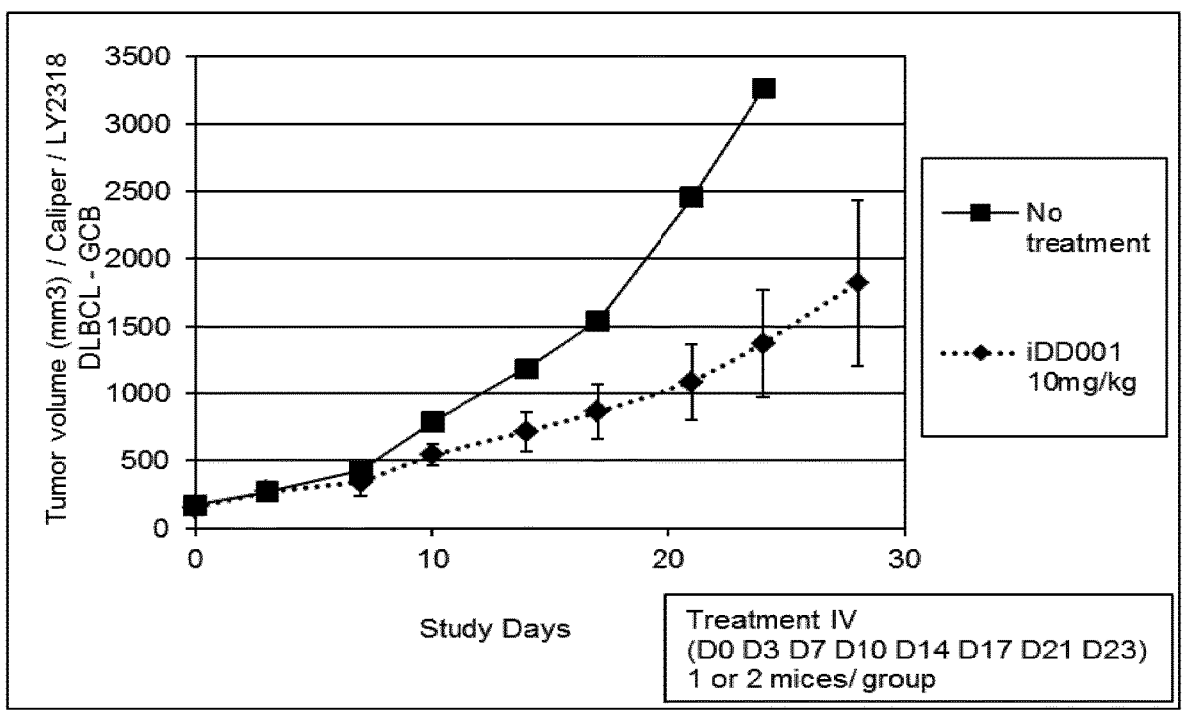

FIG. 4: In vivo inhibition of tumour growth of DLBCL subtype GCB with MAb anti-CD19/IDD001. 4A: xenograft model LY2214; 4B: xenograft model LY2318; 4C: xenograft model LY2214 with dose variations.

Figure 5:
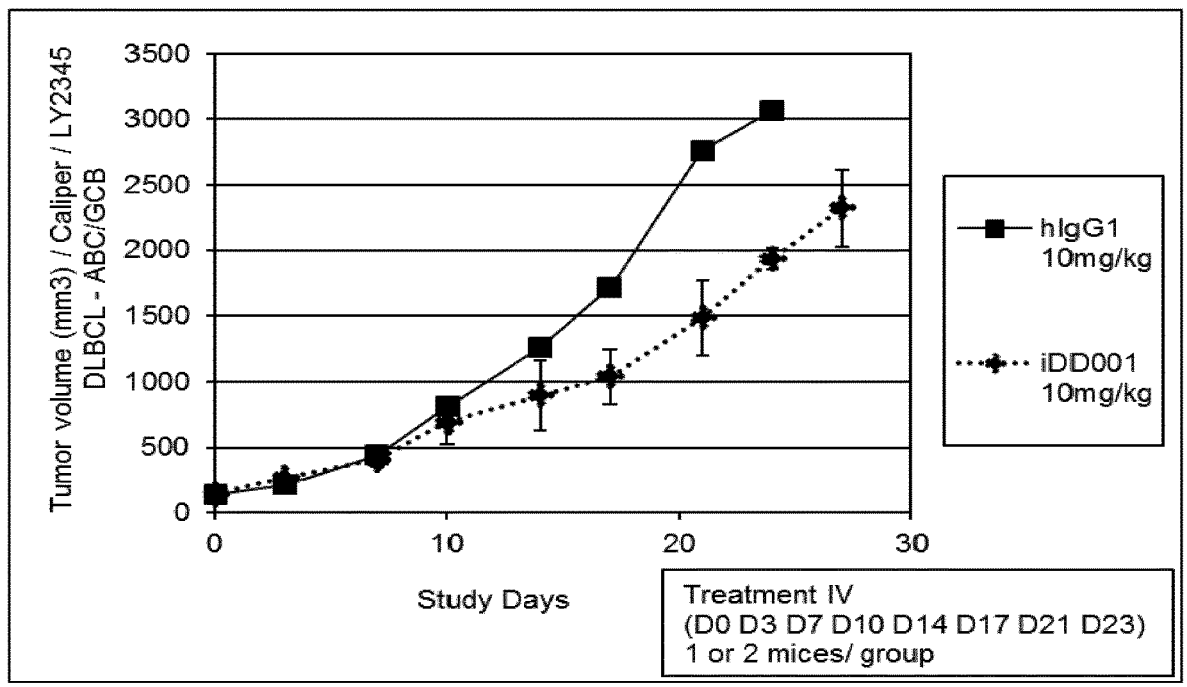
Figure 5:
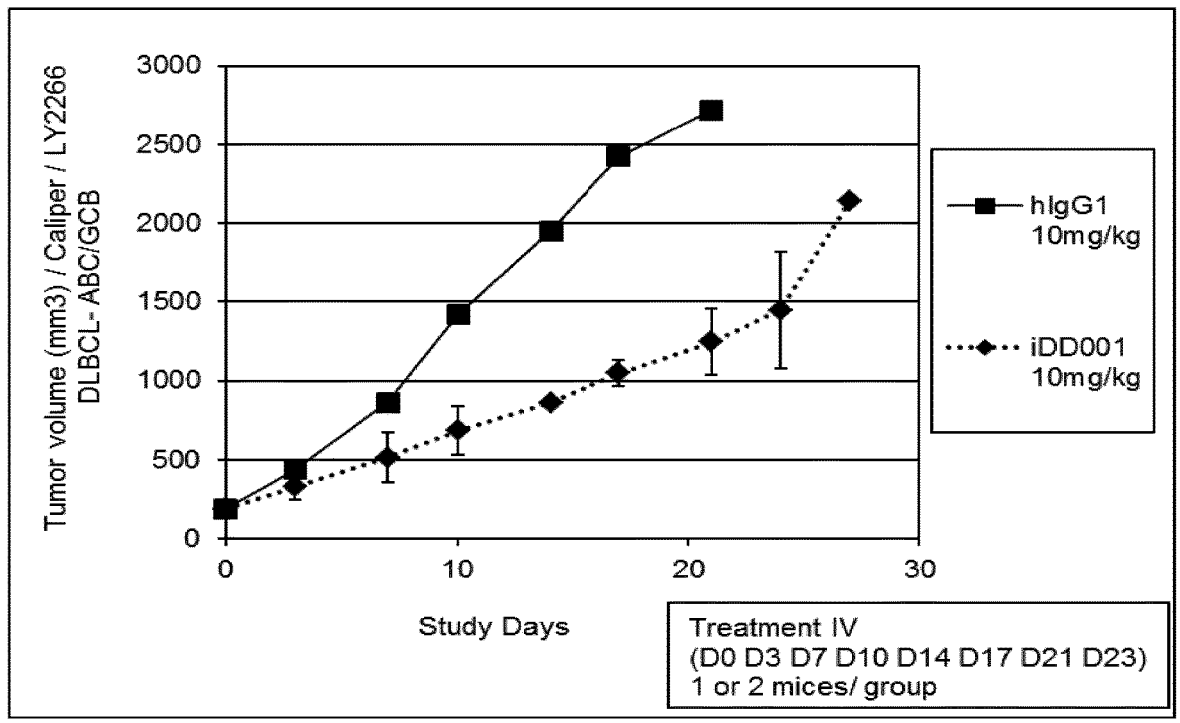

FIG. 5: In vivo inhibition of tumour growth of DLBCL subtype ABC/G CB with MAb anti-CD19/IDD001. 5A: xenograft model LY2345; 5B: xenograft model LY2266; 5C: xenograft model LY2345 with dose variations.

Figure 6:
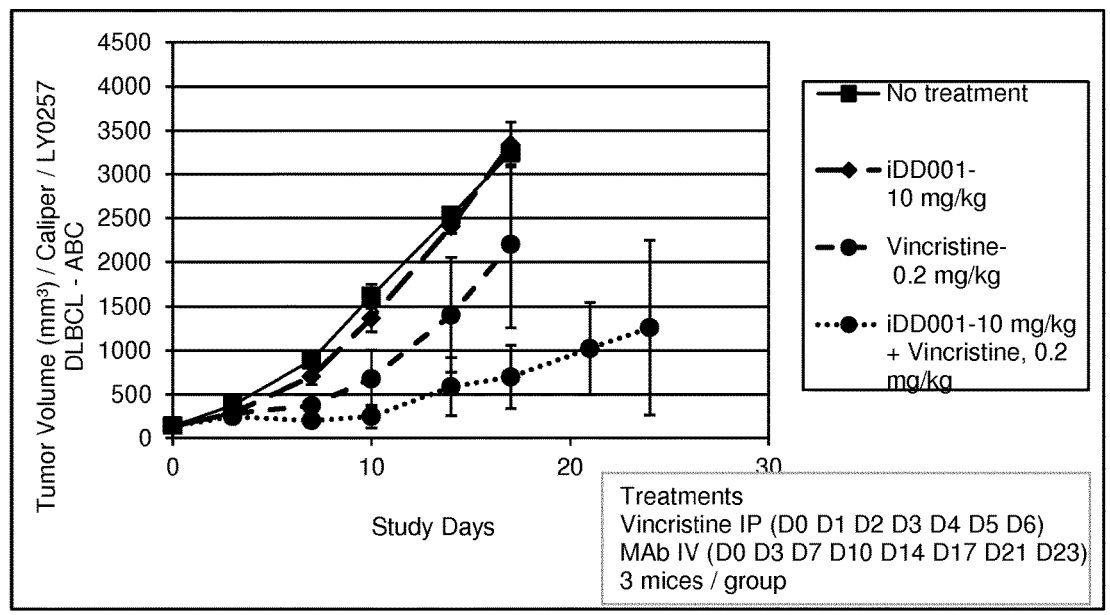

FIG. 6: In vivo inhibition of tumour growth of DLBCL ABC subtype with MAb anti-CD19/IDD001 in combination with vincristine.

Figure 7:
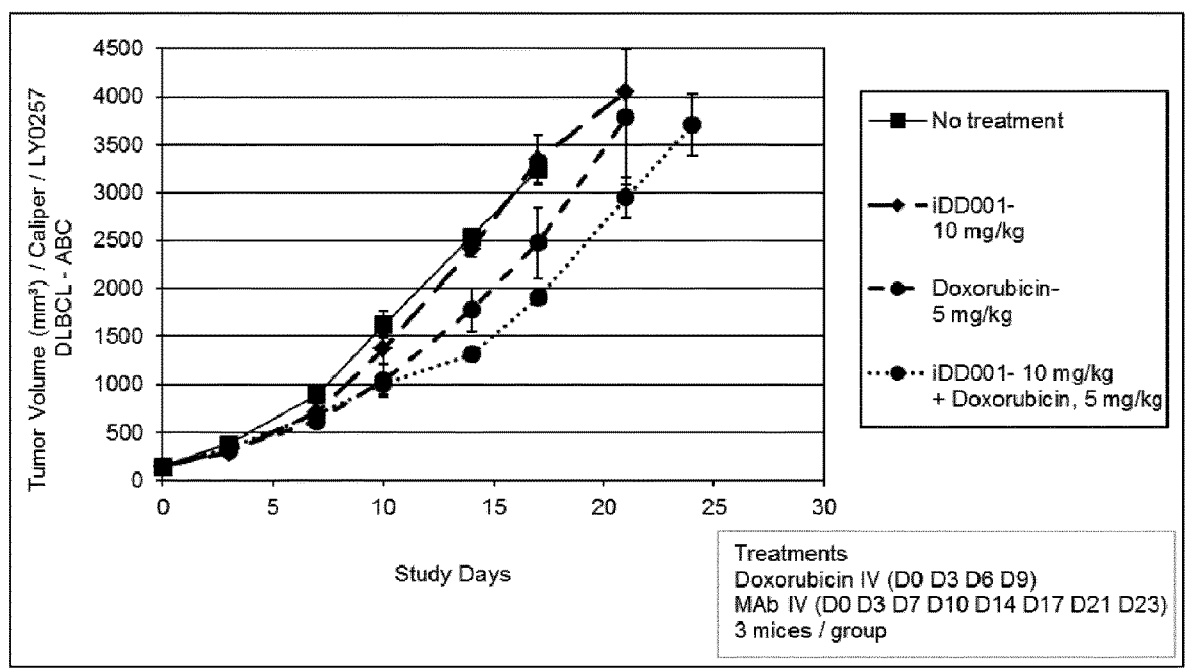

FIG. 7: In vivo inhibition of tumour growth of DLBCL ABC subtype with MAb anti-CD19/IDD001 in combination with doxorubicine.

Figure 8:
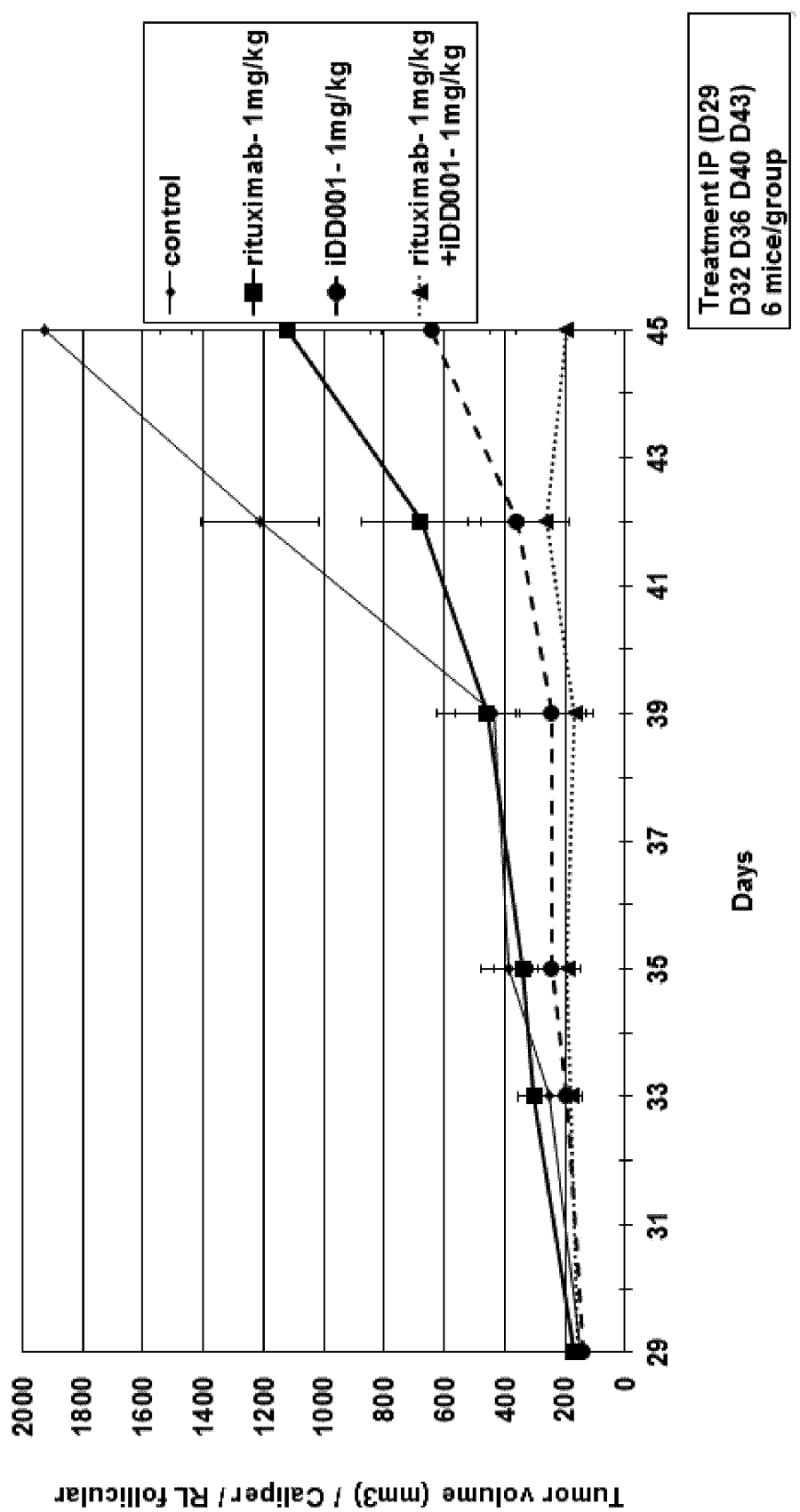

FIG. 8: In vivo inhibition of tumour growth of FL with MAb anti-CD19/IDD001 in combination with MAb anti-CD20 (rituximab)

Figure 9:
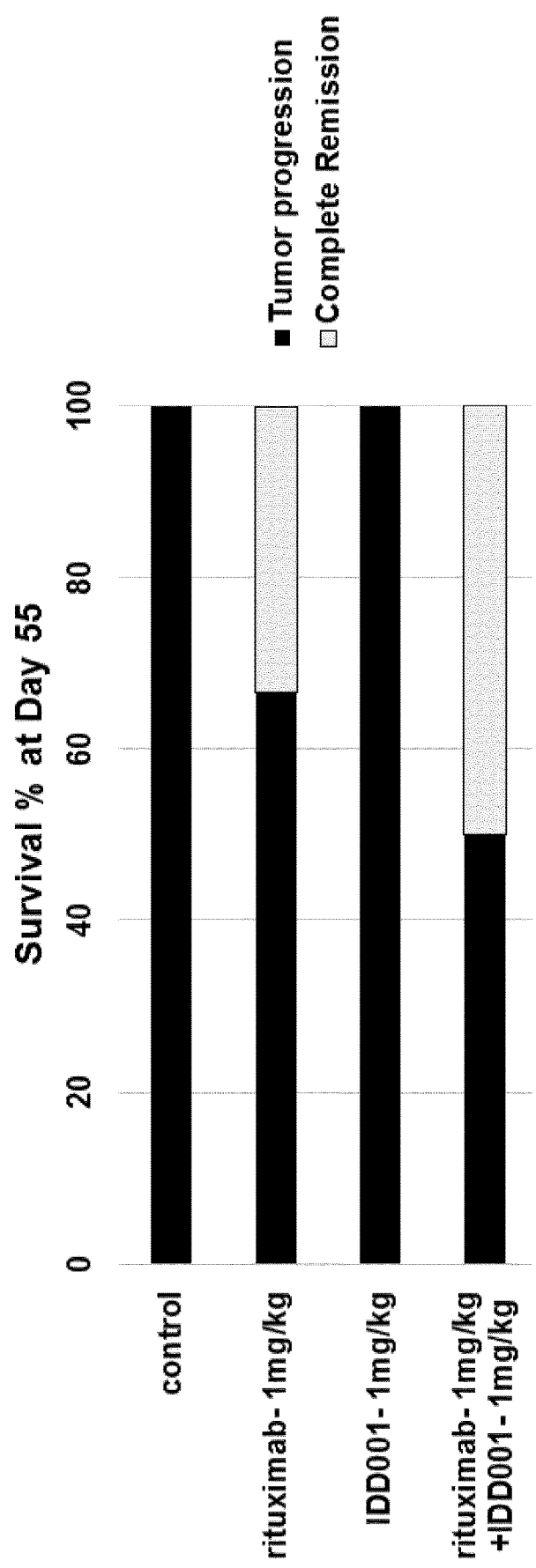

FIG. 9: Co-targeting CD19 and CD20 increases the survival percentage with lower MAb concentration.

Figure 10B:
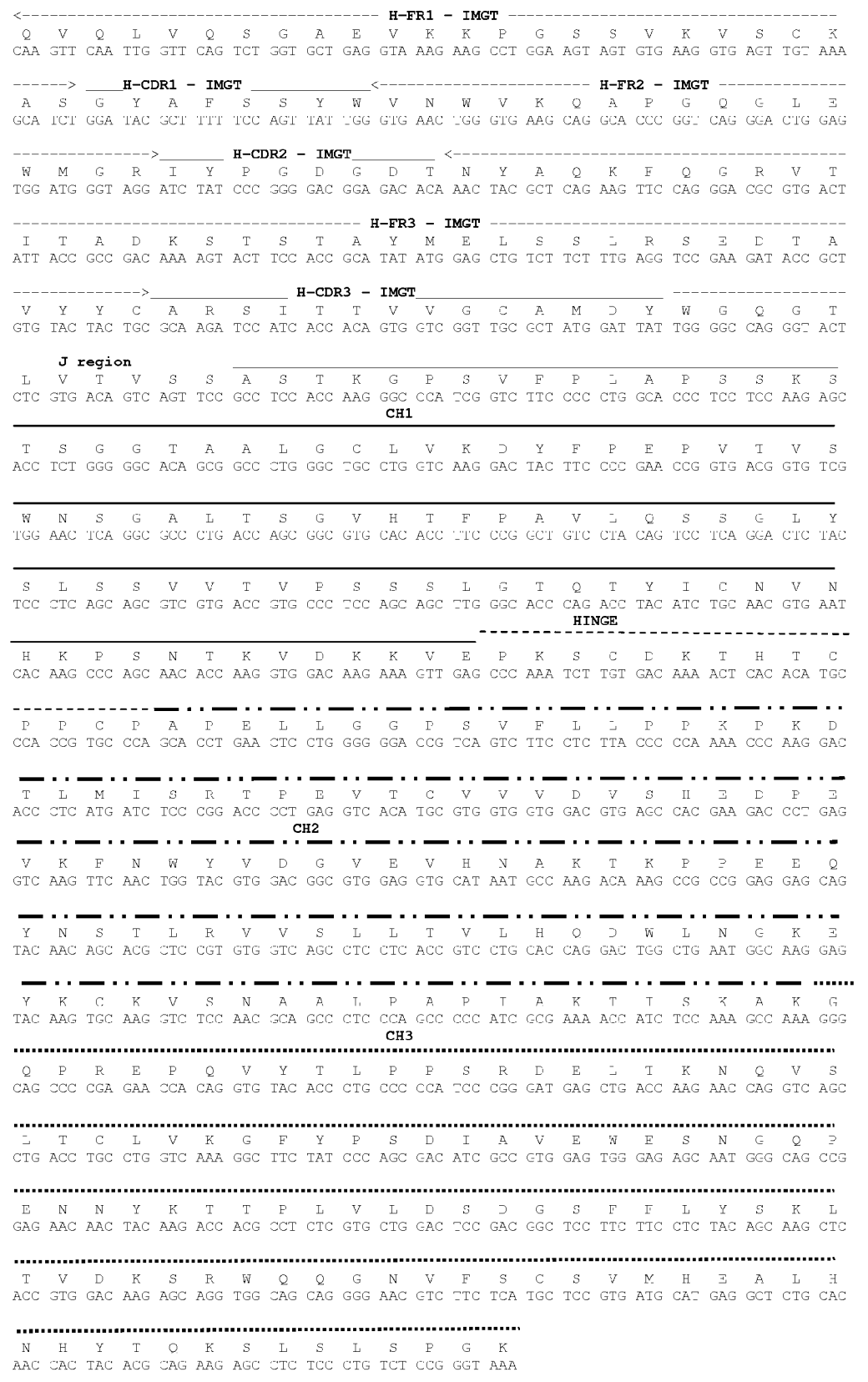

FIGS. 10A-10B: Light and Heavy humanized sequences, antibody IDD001.

Example 1: The anti-CD19 antibodies were produced as described in WO 2012/010562 or U.S. Pat. No. 9,120,856.

Figure 1A:
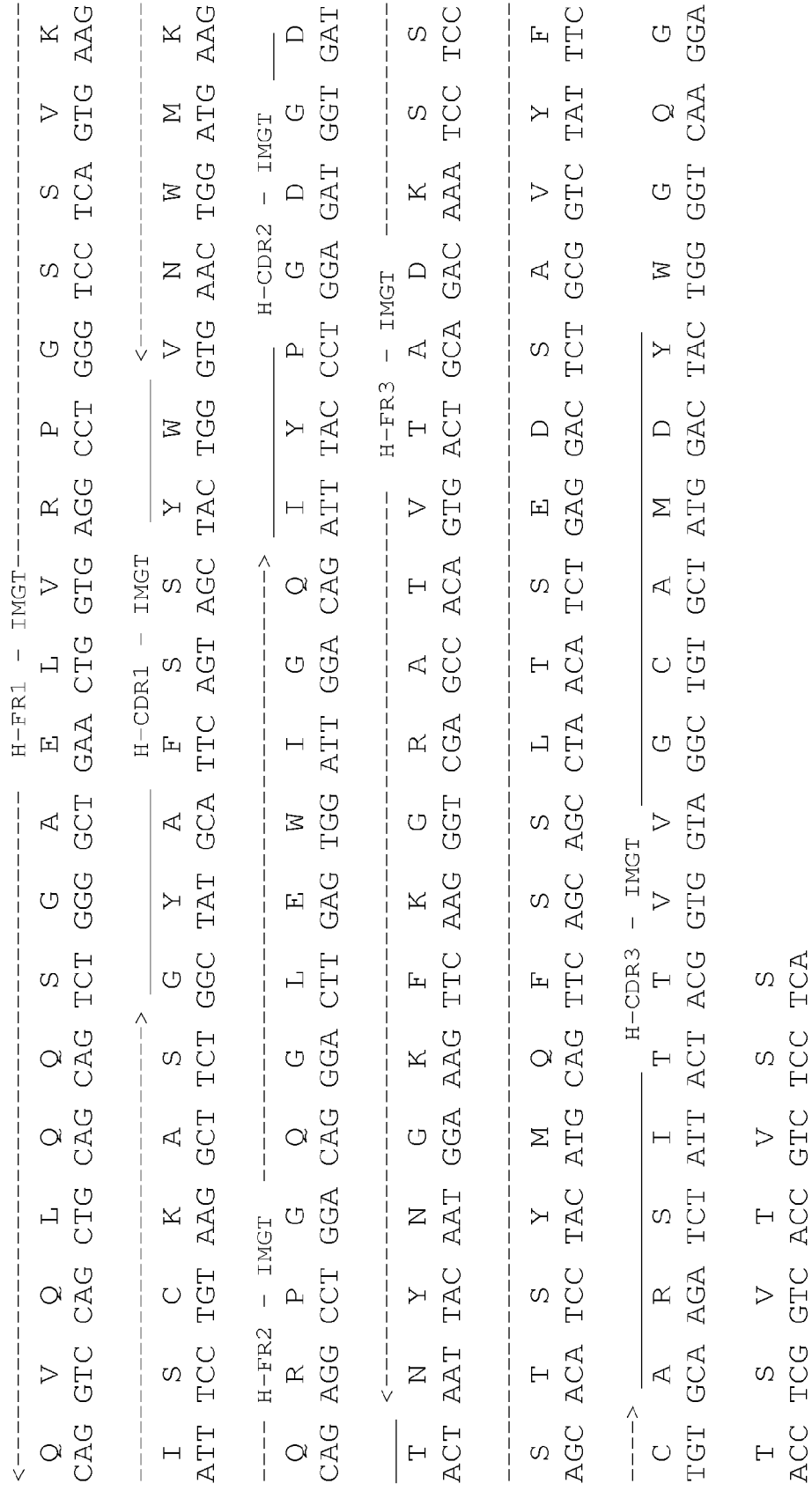
Figure 1B:
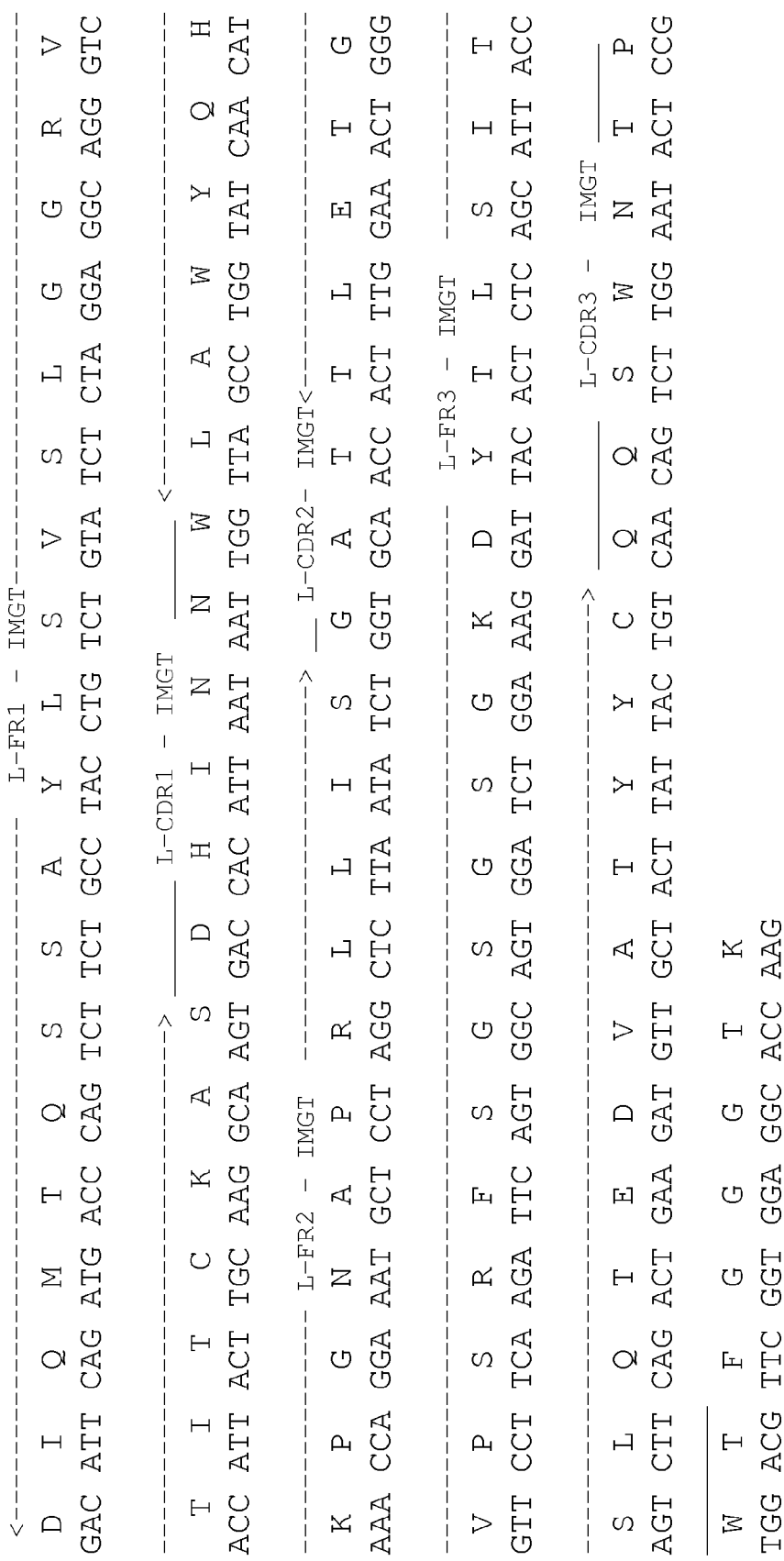
Figure 1C:
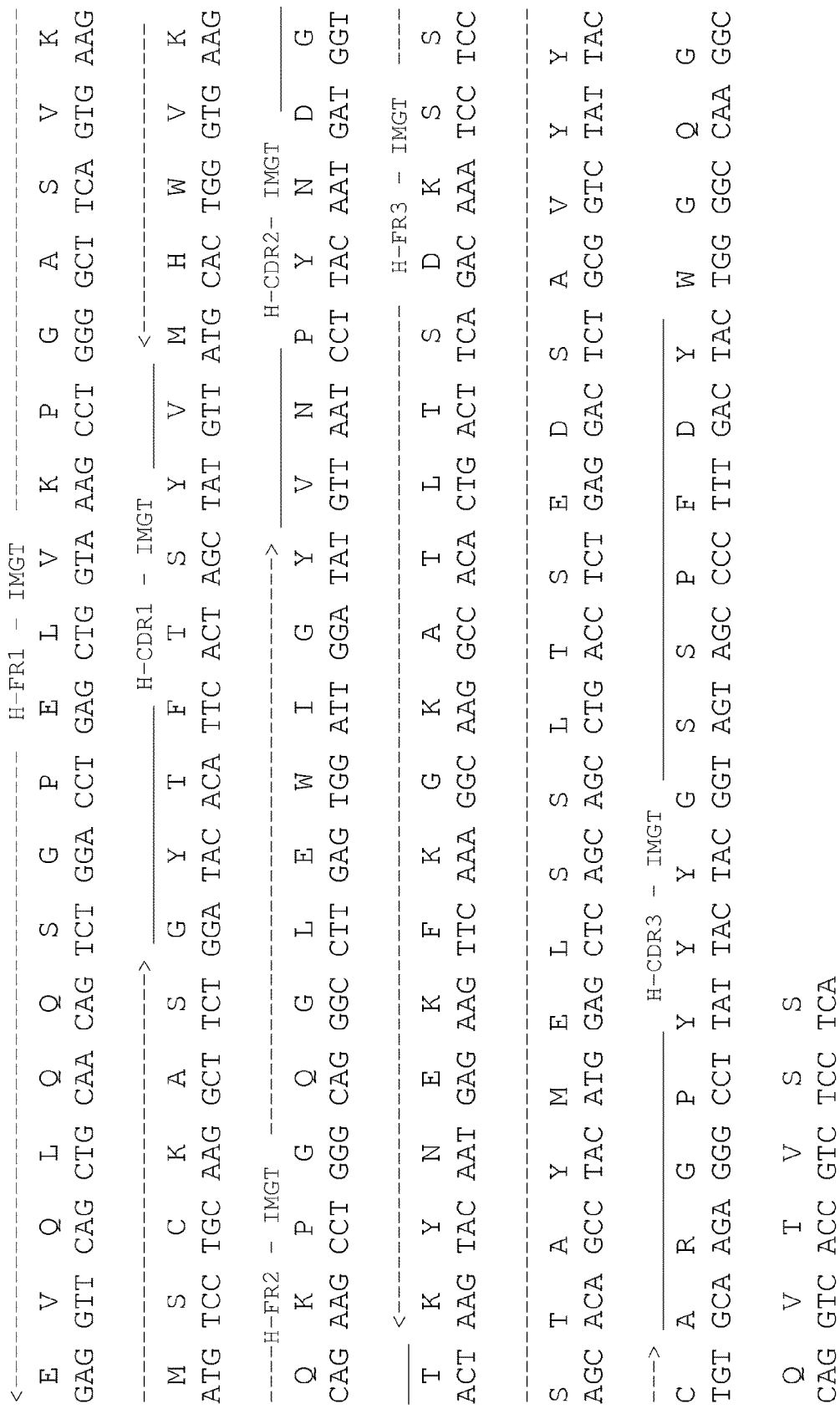

The murine MAb screening regarding the ability to trigger the highest level of programmed cell death or apoptosis was performed. Two MAbs anti CD19 were selected with the nucleotide and amino acids sequences of the murine MAbs R005-1 and R005-2 MAbs described in FIG. 1.

To improve the cancer cell depleting, Fc engineering was performed to enhance cytotoxicity potency dependent on ADCC and CDC. The amino acids and nucleic acid sequences of optimised Fc codified Fc24 (SEQ ID NO: 3 and 4) or Fc34 (SEQ ID NO: 1 and 2) variant MAb were described as one-letter codes in FIG. 2. According to the literature, the amino acid numbering of Fc region is based to the Kabat data base, (CH1: aa n° 118 to 215; Hinge: aa n° 216 to 230; CH2: aa n° 231 to 340; CH3: aa n° 341 to 447). Variations between the various Fc used in the invention with respect to native Fc (Fc0).

The full sequence of the Fc optimised humanised MAb IDD001 is described in FIG. 10.

Example 2: Different amino acid substitutions in the Fc region:

In these experiments, several alternative monoclonal antibodies were generated based on the chR005-1 Fc24 of example 1. This antibody has variable regions binding to CD19 and an IgG1 Fc region comprising the mutations F243UR292P/Y300L/V305L/K326A/E333A/P396L. Variants of this antibody have thus been prepared wherein one substitution amino acid has been changed.

These variants were assayed for CDC in the presence of human serum and ADCC in whole blood.

The results obtained are presented in a Jan. 11, 2016 Declaration under Rule 132 in the File History of U.S. application Ser. No. 13/811,134, which Declaration is incorporated herein by reference. The results show that the following variant substitutions are functional on ADCC whole blood and CDC in human serum, with no significant impact being observed with respect to the original substitution of IDD001:

F243: L could be subsituted by W, Y, R, Q, I, A
R292: P could be subsituted by G or A
V305: L (or I) could be subsituted by A
P396: L could be subsituted by I or A
Y300: L could be subsituted by K, F, I, A
K326: A could be subsituted by V, E, D, M, S, N, W
E333: A could be subsituted by V, G, D, K, S, N, R, Q.

Thus the person skilled in the art may appreciate that substitutions may be made in the Fc region while keeping substantially the effector functions of the Fc or the antibody comprising the Fc, and that these substitutions are encompassed by the present invention.

Example 3: Rituxan® (rituximab) was purchased commercially by Roche.

Example 4: Oncovin® (vincristine) was purchased commercially by Selleck (Catalog number: S1241)

Example 5: Adriamycine® (doxorubicine) was purchased commercially by Selleck (Catalog number: S1208)

Example 6: In vivo investigation on PDX models for DLBCL: Each mouse was inoculated subcutaneously at the right flank with one primary human tumor xenograft model (LY0257, LY2214, LY2264, LY2266, LY2318, LY2345 orLY3604) tumor fragment (2-3 mm in diameter) for tumour development. When average or individual tumor size reaches 100-250 mm3, mice was randomly (rolling enrollment will be involved if necessary) allocated into 3 groups. Each group contained 1 or 2 mice. The day of grouping and dosing initiation was denoted as day 0. The dosing volume was adjusted for body weight (Dosing volume=5 µL/g). After tumor inoculation, the animals were checked daily for morbidity and mortality. At the time of routine monitoring, the animals were checked for any effects of tumor growth and treatments on normal behavior such as mobility, food and water consumption, body weight gain/loss, eye/hair matting and any other abnormal effect. Death and observed clinical signs were recorded on the basis of the numbers of animals within each subset. Two weeks of dosing-free observation were applied after final treatment. The animals in vehicle group were sacrificed before study termination because of tumor volume (TV) over 3000 mm$^3$. Tumor size was measured by caliper twice weekly in two dimensions. The tumor volume was expressed in mm3 using the formula: TV=0.5 a×b2 where a and b are the long and short diameters of the tumor, respectively. Body weight was measured twice weekly. When individual mouse has a body weight loss ≥15%, the mouse was given dosing holiday(s) until its body weight recovers to body weight loss. Under following conditions, the in-life experiment of individual animal or whole groups was terminated, by human euthanization, prior to death, or before reaching a comatose state.

DLBCL in vivo proof of concept from patient derivates (PDX models): 7 HuPrime® lymphoma xenograft models (selected in CRO cell bank CD19+ for cDNA), LY0257, LY2214, LY2264, LY2266, LY2318, LY2345 and LY3604, were selected. The cancer subtype of those models is listed in the table below.

TABLE 1

Study design of MAb impact regarding DLBCL subtype

| Model nomenclature | Subtype |
|---|---|
| LY0257 | NHL (DLBCL, ABC, MYD88 L265P) |
| LY2214 | NHL (DLBCL, GCB) |
| LY2264 | NHL (DLBCL, ABC, MYD88 L265P) |
| LY2266 | NHL (B cell, ABC/GCB) |
| LY2318 | NHL (DLBCL, GCB) |
| LY2345 | NHL (DLBCL, ABC/GCB) |
| LY3604 | NHL (DLBCL, ABC) |

Study design for MAb impact regarding DLBCL subtypes
Seven HuPrime® DLBCL lymphoma xenograft models as ABC (LY0257, LY2264, LY3604), GCB (LY2214, LY2318) or ABC/GCB (LY2345, LY2266) were tested.

TABLE 2

Study design of MAb impact regarding DLBCL subtype

| Group | N | Treatment | Dose level (mg/kg) | Dose Route | Dosing Frequency |
|---|---|---|---|---|---|
| 1 | 1 | No treatment or irrelevant human IgG | NA | NA | BIW × 4 |
| 2 | 2 | IDD001 MAb anti CD19 | 10 | i.v. | BIW × 4 |

N: animal number per group

Study design for MAb dose effect according the DLBCL subtypes Three HuPrime® DLBCL lymphoma xenograft models as ABC (LY2264), GCB (LY2214), or ABC/GCB (LY2345) were tested.

TABLE 3

Study design of MAb dosing efficacy study for ABC/LY2264 and GCB/LY2214 in Nod SCID mice

| Group | N | Treatment | Dose level (mg/kg) | Dose Route | Dosing Frequency |
|---|---|---|---|---|---|
| 1 | 3 | No treatment or irrelevant human IgG | — | — | BIW × 4 |
| 2 | 3 | IDD001 | 10 | i.v. | BIW × 4 |
| 3 | 3 | MAb anti | 1 | i.v. | BIW × 4 |
| 4 | 3 | CD19 | 0.1 | i.v. | BIW × 4 |

TABLE 4

Study design of of MAb dosing efficacy study for ABC/GCB LY2345 in NPG mice

| Group | N | Treatment | Dose level (mg/kg) | Dose Route | Dosing Frequency |
|---|---|---|---|---|---|
| 1 | 3 | No treatment or irrelevant human IgG | — | — | BIW × 4 |
| 2 | 3 | IDD001 | 10 | i.v. | BIW × 4 |
| 3 | 3 | MAb anti | 25 | i.v. | BIW × 4 |
| 4 | 3 | CD19 | 50 | i.v. | BIW × 4 |

Note:
N: animal number per group

Study design for Combitherapy for DLBCL ABC subtype
The HuPrime® DLBCL lymphoma xenograft model ABC (LY0257) was tested.

TABLE 5

Study design of combitherapy for LY0257 in BALB/c nude mice

| Group | N | Treatment | Dose level (mg/kg) | Dose Route | Dosing Frequency |
|---|---|---|---|---|---|
| 1 | 3 | | — | — | BIW × 4 |
| 2 | 3 | IDD001 MAb anti CD19 | 10 | i.v. | BIW × 4 |
| 3 | 3 | Vincristine | 0.2 | i.p. | QD × 7 |
| 4 | 3 | Doxorubicin | 5 | i.v. | Q3D × 4 |
| 5 | 3 | IDD001 MAb anti CD19 Vincristine | 10 / 0.2 | i.v. / i.p. | BIW.4 / QD × 7 |
| 6 | 3 | IDD001 MAb anti CD19 Doxorubicin | 10 / 5 | i.v. / i.v. | BIW × 4 / Q3D × 4 |

In vivo inhibition of tumor growth of DLBCL subtypes with MAb anti-CD19

Results show in FIG. 3 revealed that DLBCL-ABC lymphoma was reduced partially as exemplified from three independent human tumors in PDX grafted mice produced. 3A: xenograft model LY0257; 3B: xenograft model LY2264; 3C: xenograft model LY3604. Following the dose-dependent manner, IDD001 mediated cytotoxicity of LY2264 PDX model was very sensitive at the highest MAb dose of 10 mg/kg. 3D: xenograft model LY2264 with dose variations.

Results show in FIG. 4 revealed that IDD001 mediated cytotoxicity against two DLBCL-GCB lymphoma at varying degrees of cell killing. The LY2214 PDX model was very sensitive, whereas the LY2318 PDX model was moderately sensitive. 4A: xenograft model LY2214; 4B: xenograft model LY2318. Following the dose-dependent manner, IDD001 mediated cytotoxicity of LY2214 PDX model was very sensitive at the highest MAb dose of 10 mg/kg. 4C: xenograft model LY2214 with dose variations.

Results show in FIG. 5 revealed that DLBCL-ABC/GCB lymphoma was reduced partially 5A: xenograft model LY2345; 5B: xenograft model LY2266. Even at highest MAb concentration (50 mg/ml), no complete tumor regression was observed. 5C: xenograft model LY2345 with dose variations.

In vivo inhibition of tumor growth of Diffuse Large B cell lymphoma (DLBCL) subtypes with combitherapy based on MAb anti-CD19 and chemodrugs In order to enhance tumor regression, the cytotoxic effects of a combination of IDD001 and Vincristine were presented in FIG. 6. The combitherapy with IDD001 and vincristine of LY0257 DLBCL-ABC model produced synergistic cell killing compared with either single agent.

By contrast results show in FIG. 7 revealed that no similar stronger growth tumor control was observed following the combitherapy with IDD001 and doxorubicine of LY0257 DLBCL-ABC model.

Example 7: In vivo investigation on CDX models for FL
Human follicular cell line RL was subcutaneously injected in SCID mice, with a concentration of $5.10^6$ cells per injection (200 μL). Mice were randomized when the tumors reached a mean volume of about 100 mm$^3$ for the 9 groups (total 45 mice). All the mice were observed in order to detect any toxic effects of the product. The endpoint was defined by animal ethics as a tumor diameter of >18 mm, significant weight loss or alteration of animal well-being. In order to assess the effectiveness of the compounds on tumorigenesis, tumor volume was measured two times a week. The sizes of the primary tumors were measured using calipers and the tumor volume (TV) was extrapolated to a sphere using the formula TV=4/3 λ×r$^3$, by calculating the mean radius from the two measurements. The median and standard deviation were also calculated for each group. Median is preferred to mean in order to exclude the extreme values. MAb treatment was administered by intraperitoneal injection twice a week during three weeks at 30, 10 or 1 mg/kg doses. The product was prepared in accordance with the sponsor's guidelines, i.e. diluted in PBS. Mice were sacrificed when the tumors reached a maximum volume of 1600 mm³. The endpoints were defined by clinical trial ethics as a tumor diameter of >18 mm or weight loss of >10% of body weight, or when the tumors are dangerous for mice (necrosis). Statistical analysis was performed with GraphPad Prism software. GraphPad Prism combined scientific graphing, comprehensive curve fitting, understandable statistics, and data organization. The t-test (two-tailed test) was performed on the tumor volume values (mm³) measured on the day of sacrifice.

Results shown in FIG. 8 that the combination treatment resulted in additive cytotoxicity of tumour growth of FL with MAb anti-CD19/IDD001 in combination with MAb anti-CD20 (rituximab).

Co-targeting CD19 and CD20 increased the survival percentage. Whereas 33% of mice treated with rituximab at 1 mg/kg are in complete remission, 50% mice treated with rituximab and IDD001 are in complete remission at day 45. Detailed values of survival at day 55 are presented in the following table:

| Identification | Tumor progression | Complete Remission |
| --- | --- | --- |
| Day | 55 | 55 |
| control | 100 | 0 |
| rituximab-1 mg/kg | 67 | 33 |
| IDD001-1 mg/kg | 100 | 0 |
| rituximab-1 mg/kg +IDD001-1 mg/kg | 50 | 50 |

The invention will now be described by the following numbered paragraphs: 1- A pharmaceutical composition comprising an anti-CD19 antibody which comprises (i) the CDRs of one of the antibodies R005-1, R005-2 or IDD001 whose VH and VL amino acid sequences are depicted on the following table,

| | Amino acid sequence VH | Amino acid sequence VL |
| --- | --- | --- |
| R005-1 | SEQ ID NO: 29 | SEQ ID NO: 31 |
| R005-2 | SEQ ID NO: 33 | SEQ ID NO: 35 |
| IDD001 | SEQ ID NO: 39 | SEQ ID NO: 37 |

(2i) a variant human IgG1 Fc region, wherein this variant region comprises an amino acid substitution at each of the amino acid positions 243, 292, 300, 305, 396, or 243, 292, 300, 305, 326, 396 or 243, 292, 300, 305, 326, 333, 396 of the human IgG Fc region, wherein the numbering of the amino acid residues in the Fc region is the one of the Kabat, for use in treating Diffuse Large B Cell Lymphoma (DLBCL) expressing CD19 or Follicular Lymphoma (FL) expressing CD19 in a patient in need thereof.

2—A combination of (1) an anti-CD19 antibody comprising (i) the CDRs of one of the antibodies R005-1, R005-2 or IDD001 whose VH and VL amino acid sequences are depicted on the following table,

| | Amino acid sequence VH | Amino acid sequence VL |
| --- | --- | --- |
| R005-1 | SEQ ID NO: 29 | SEQ ID NO: 31 |
| R005-2 | SEQ ID NO: 33 | SEQ ID NO: 35 |
| IDD001 | SEQ ID NO: 39 | SEQ ID NO: 37 |

(2i) a variant human IgG1 Fc region, wherein this variant region comprises an amino acid substitution at each of the amino acid positions 243, 292, 300, 305, 396, or 243, 292, 300, 305, 326, 396 or 243, 292, 300, 305, 326, 333, 396 of the human IgG Fc region, wherein the numbering of the amino acid residues in the Fc region is the one of the Kabat, and (2) a chemotherapeutic drug of the vinca alcloid group, for use in treating Diffuse Large B Cell Lymphoma (DLBCL) expressing CD19 in a patient in need thereof.

3—The combination for the use of paragraph 2, wherein the chemotherapeutic drug is vincristine.

4—The combination for the use of paragraph 2 or 3, which is for use to treat DLBCL subtype GCB, ABC or ABC/GCB.

5—The combination for the use of any one of paragraphs 2 to 4, which is for use in combination with vincristine to treat DLBCL subtype ABC or GCB or ABC/GCB, wherein the combined use of the antibody and the chemotherapeutic drug is simultaneous, separate or sequential.

6—The combination for the use of any one of paragraphs 2 to 5, wherein the anti-CD19 antibody in combination with vincristine leads to higher rate of regression compared with either single agent.

7—A combination of (1) an anti-CD19 antibody comprising (i) the CDRs of one of the antibodies R005-1, R005-2 or IDD001 whose VH and VL amino acid sequences are depicted on the following table,

| | Amino acid sequence VH | Amino acid sequence VL |
| --- | --- | --- |
| R005-1 | SEQ ID NO: 29 | SEQ ID NO: 31 |
| R005-2 | SEQ ID NO: 33 | SEQ ID NO: 35 |
| IDD001 | SEQ ID NO: 39 | SEQ ID NO: 37 |

(2i) a variant human IgG1 Fc region, wherein this variant region comprises an amino acid substitution at each of the amino acid positions 243, 292, 300, 305, 396, or 243, 292, 300, 305, 326, 396 or 243, 292, 300, 305, 326, 333, 396 of the human IgG Fc region, wherein the numbering of the amino acid residues in the Fc region is the one of the Kabat, and (2) an anti-CD20 antibody for use in treating Follicular Lymphoma (FL) expressing CD19 and CD20 in a patient in need thereof.

8—The combination for the use of paragraph 8, wherein the anti-CD20 antibody is rituxan.

9—The combination for the use of paragraph 7 or, wherein the combination of both antibodies leads to a higher rate of regression or remission compared with either single agent.

10—The combination for the use of any one of paragraphs 2 to 9, wherein the anti-CD19 antibody comprises VH and VL amino acid sequences are depicted on the following table,

| | Amino acid sequence VH | Amino acid sequence VL |
| --- | --- | --- |
| R005-1 | SEQ ID NO: 29 | SEQ ID NO: 31 |
| R005-2 | SEQ ID NO: 33 | SEQ ID NO: 35 |
| IDD001 | SEQ ID NO: 39 | SEQ ID NO: 37 |

11—The composition or combination for the use of any one of paragraphs 1 to 10, wherein the antibody comprises an Fc region in which Phe243 is substituted by Leu, Arg292 is substituted by Pro, Tyr300 is substituted by Leu, Val305 is substituted by Leu or Ile, Lys326 is substituted by Ala and Pro396 is substituted by Leu.

12—The composition or combination for the use of any one of paragraphs 1 to 10, wherein the antibody comprises an Fc region in which Phe243 is substituted by Leu, Arg292 is substituted by Pro, Tyr300 is substituted by Leu, Val305 is substituted by Leu or Ile, Lys326 is substituted by Ala and Pro396 is substituted by Leu, and Glu333 is substituted by Ala.

13—Humanized monoclonal anti-CD19 antibody, having the VH sequence SEQ ID NO: 39 and the VL sequence SEQ ID NO: 37.

The invention claimed is:

1. Humanized monoclonal anti-CD19 antibody, having the following CDRs:

| | SEQ ID NO: | Sequence IMGT | SEQ ID NO: | Sequence Kabat | SEQ ID NO: | Sequence (Common numbering system) |
|---|---|---|---|---|---|---|
| VH IDD001 | | | | | | |
| CDR1 | 5 | GYAFSSYW | 11 | SYWVN | 16 | SSYW |
| CDR2 | 6 | IYPGDGDT | 12 | QIYPGDGDTNYNGKFKG | 6 | IYPGDGDT |
| CDR3 | 7 | ARSITTVVGCAMDY | 13 | SITTVVGCAMDY | 13 | SITTVVGCAMDY |
| VL IDD001 | | | | | | |
| CDR1 | 41 | QSINNW | 42 | KASQSINNWLA | 41 | QSINNW |
| CDR2 | 43 | GAS | 44 | GASTLET | 43 | GAS |
| CDR3 | 10 | QQSWNTPWT | 10 | QQSWNTPWT | 10 | QQSWNTPWT. |

2. The humanized monoclonal anti-CD19 antibody of claim 1, having the VH sequence 1-121 of SEQ ID NO: 39 and the VL sequence 1-103 of SEQ ID NO: 37.

3. The humanized monoclonal anti-CD19 antibody of claim 1, having a Heavy Chain of SEQ ID NO: 39 and a Light Chain of SEQ ID NO: 37.

4. A method for treating Diffuse Large B Cell Lymphoma (DLBCL) in a patient in need thereof, comprising administering an efficient amount of a monoclonal antibody according to claim 1.

5. The method of claim 4, wherein said antibody has the VH sequence 1-121 of SEQ ID NO: 39 and the VL sequence 1-103 of SEQ ID NO: 37.

6. The method of claim 4, wherein said antibody has a Heavy Chain of SEQ ID NO: 39 and a Light Chain of SEQ ID NO: 37.

7. A method for treating Follicular Lymphoma (FL) in a patient in need thereof, comprising administering an efficient amount of a monoclonal antibody according to claim 1.

8. A method of claim 7, wherein said antibody has the VH sequence 1-121 of SEQ ID NO: 39 and the VL sequence 1-103 of SEQ ID NO: 37.

9. A method of claim 7, wherein said antibody has a Heavy Chain of SEQ ID NO: 39 and a Light Chain of SEQ ID NO: 37.

* * * * *

SEQUENCE LISTING

```
<160> NUMBER OF SEQ ID NOS: 44

<210> SEQ ID NO 1
<211> LENGTH: 330
<212> TYPE: PRT
<213> ORGANISM: artificial sequence
<220> FEATURE:
<223> OTHER INFORMATION: Fc34

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Leu Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Pro Glu
                165                 170                 175

Glu Gln Tyr Asn Ser Thr Leu Arg Val Val Ser Leu Leu Thr Val Leu
            180                 185                 190

His Gln Asp Trp Leu Asn Gly Lys Glu Tyr Lys Cys Lys Val Ser Asn
        195                 200                 205

Ala Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Leu Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 993
<212> TYPE: DNA
<213> ORGANISM: artificial sequence
<220> FEATURE:
<223> OTHER INFORMATION: Fc34

<400> SEQUENCE: 2

```
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtcgtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttacc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcggagga gcagtacaac     540
agcacgctcc gtgtggtcag cctcctcacc gtcctgcacc aggactggct gaatggcaag     600
gagtacaagt gcaaggtctc caacgcagcc ctcccagccc catcgagaa aaccatctcc     660
aaagccaaag gcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctctcgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa tga                                  993
```

<210> SEQ ID NO 3
<211> LENGTH: 330
<212> TYPE: PRT
<213> ORGANISM: artificial sequence
<220> FEATURE:
<223> OTHER INFORMATION: Fc24

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Leu Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Leu Arg Val Val Ser Leu Leu Thr Val Leu
            180                 185                 190

His Gln Asp Trp Leu Asn Gly Lys Glu Tyr Lys Cys Lys Val Ser Asn
        195                 200                 205

Ala Ala Leu Pro Ala Pro Ile Ala Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Leu Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 4
<211> LENGTH: 993
<212> TYPE: DNA
<213> ORGANISM: artificial sequence
<220> FEATURE:
<223> OTHER INFORMATION: Fc24

<400> SEQUENCE: 4
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtcgtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttacc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgccggagga gcagtacaac     540
agcacgctcc gtgtggtcag cctcctcacc gtcctgcacc aggactggct gaatggcaag     600
gagtacaagt gcaaggtctc caacgcagcc ctcccagccc ccatcgcgaa aaccatctcc     660
aaagccaaag ggcagccccg agaaccacag gtgtacaccc tgcccccatc ccgggatgag     720
```

```
ctgaccaaga accaggtcag cctgacctgc ctggtcaaag gcttctatcc cagcgacatc      780
gccgtggagt gggagagcaa tgggcagccg gagaacaact acaagaccac gcctctcgtg      840
ctggactccg acggctcctt cttcctctac agcaagctca ccgtggacaa gagcaggtgg      900
cagcagggga acgtcttctc atgctccgtg atgcatgagg ctctgcacaa ccactacacg      960
cagaagagcc tctccctgtc tccgggtaaa tga                                   993
```

<210> SEQ ID NO 5
<211> LENGTH: 8
<212> TYPE: PRT
<213> ORGANISM: artificial sequence
<220> FEATURE:
<223> OTHER INFORMATION: peptide

<400> SEQUENCE: 5

Gly Tyr Ala Phe Ser Ser Tyr Trp
1               5

<210> SEQ ID NO 6
<211> LENGTH: 8
<212> TYPE: PRT
<213> ORGANISM: artificial sequence
<220> FEATURE:
<223> OTHER INFORMATION: peptide

<400> SEQUENCE: 6

Ile Tyr Pro Gly Asp Gly Asp Thr
1               5

<210> SEQ ID NO 7
<211> LENGTH: 14
<212> TYPE: PRT
<213> ORGANISM: artificial sequence
<220> FEATURE:
<223> OTHER INFORMATION: peptide

<400> SEQUENCE: 7

Ala Arg Ser Ile Thr Thr Val Val Gly Cys Ala Met Asp Tyr
1               5                   10

<210> SEQ ID NO 8
<211> LENGTH: 6
<212> TYPE: PRT
<213> ORGANISM: artificial sequence
<220> FEATURE:
<223> OTHER INFORMATION: peptide

<400> SEQUENCE: 8

Asp His Ile Asn Asn Trp
1               5

<210> SEQ ID NO 9
<211> LENGTH: 3
<212> TYPE: PRT
<213> ORGANISM: artificial sequence
<220> FEATURE:
<223> OTHER INFORMATION: peptide

<400> SEQUENCE: 9

Gly Ala Thr
1

<210> SEQ ID NO 10
<211> LENGTH: 9
<212> TYPE: PRT

```
<213> ORGANISM: artificial sequence
<220> FEATURE:
<223> OTHER INFORMATION: peptide

<400> SEQUENCE: 10

Gln Gln Ser Trp Asn Thr Pro Trp Thr
1               5

<210> SEQ ID NO 11
<211> LENGTH: 5
<212> TYPE: PRT
<213> ORGANISM: artificial sequence
<220> FEATURE:
<223> OTHER INFORMATION: peptide

<400> SEQUENCE: 11

Ser Tyr Trp Val Asn
1               5

<210> SEQ ID NO 12
<211> LENGTH: 17
<212> TYPE: PRT
<213> ORGANISM: artificial sequence
<220> FEATURE:
<223> OTHER INFORMATION: peptide

<400> SEQUENCE: 12

Gln Ile Tyr Pro Gly Asp Gly Asp Thr Asn Tyr Asn Gly Lys Phe Lys
1               5                   10                  15

Gly

<210> SEQ ID NO 13
<211> LENGTH: 12
<212> TYPE: PRT
<213> ORGANISM: artificial sequence
<220> FEATURE:
<223> OTHER INFORMATION: peptide

<400> SEQUENCE: 13

Ser Ile Thr Thr Val Val Gly Cys Ala Met Asp Tyr
1               5                   10

<210> SEQ ID NO 14
<211> LENGTH: 11
<212> TYPE: PRT
<213> ORGANISM: artificial sequence
<220> FEATURE:
<223> OTHER INFORMATION: peptide

<400> SEQUENCE: 14

Lys Ala Ser Asp His Ile Asn Asn Trp Leu Ala
1               5                   10

<210> SEQ ID NO 15
<211> LENGTH: 7
<212> TYPE: PRT
<213> ORGANISM: artificial sequence
<220> FEATURE:
<223> OTHER INFORMATION: peptide

<400> SEQUENCE: 15

Gly Ala Thr Thr Leu Glu Thr
1               5

<210> SEQ ID NO 16
<211> LENGTH: 4
```

```
<212> TYPE: PRT
<213> ORGANISM: artificial sequence
<220> FEATURE:
<223> OTHER INFORMATION: peptide

<400> SEQUENCE: 16

Ser Ser Tyr Trp
1

<210> SEQ ID NO 17
<211> LENGTH: 8
<212> TYPE: PRT
<213> ORGANISM: artificial sequence
<220> FEATURE:
<223> OTHER INFORMATION: peptide

<400> SEQUENCE: 17

Gly Tyr Thr Phe Thr Ser Tyr Val
1               5

<210> SEQ ID NO 18
<211> LENGTH: 8
<212> TYPE: PRT
<213> ORGANISM: artificial sequence
<220> FEATURE:
<223> OTHER INFORMATION: peptide

<400> SEQUENCE: 18

Val Asn Pro Tyr Asn Asp Gly Thr
1               5

<210> SEQ ID NO 19
<211> LENGTH: 14
<212> TYPE: PRT
<213> ORGANISM: artificial sequence
<220> FEATURE:
<223> OTHER INFORMATION: peptide

<400> SEQUENCE: 19

Ala Arg Gly Pro Tyr Tyr Tyr Gly Ser Ser Pro Phe Asp Tyr
1               5                   10

<210> SEQ ID NO 20
<211> LENGTH: 11
<212> TYPE: PRT
<213> ORGANISM: artificial sequence
<220> FEATURE:
<223> OTHER INFORMATION: peptide

<400> SEQUENCE: 20

Gln Ser Leu Glu Asn Ser Asn Gly Asn Thr Tyr
1               5                   10

<210> SEQ ID NO 21
<211> LENGTH: 3
<212> TYPE: PRT
<213> ORGANISM: artificial sequence
<220> FEATURE:
<223> OTHER INFORMATION: peptide

<400> SEQUENCE: 21

Arg Val Ser
1

<210> SEQ ID NO 22
<211> LENGTH: 9
<212> TYPE: PRT
```

```
<213> ORGANISM: artificial sequence
<220> FEATURE:
<223> OTHER INFORMATION: peptide

<400> SEQUENCE: 22

Leu Gln Val Thr His Val Pro Pro Thr
1               5

<210> SEQ ID NO 23
<211> LENGTH: 5
<212> TYPE: PRT
<213> ORGANISM: artificial sequence
<220> FEATURE:
<223> OTHER INFORMATION: peptide

<400> SEQUENCE: 23

Ser Tyr Val Met His
1               5

<210> SEQ ID NO 24
<211> LENGTH: 17
<212> TYPE: PRT
<213> ORGANISM: artificial sequence
<220> FEATURE:
<223> OTHER INFORMATION: peptide

<400> SEQUENCE: 24

Tyr Val Asn Pro Tyr Asn Asp Gly Thr Lys Tyr Asn Glu Lys Phe Lys
1               5                   10                  15

Gly

<210> SEQ ID NO 25
<211> LENGTH: 12
<212> TYPE: PRT
<213> ORGANISM: artificial sequence
<220> FEATURE:
<223> OTHER INFORMATION: peptide

<400> SEQUENCE: 25

Gly Pro Tyr Tyr Tyr Gly Ser Ser Pro Phe Asp Tyr
1               5                   10

<210> SEQ ID NO 26
<211> LENGTH: 16
<212> TYPE: PRT
<213> ORGANISM: artificial sequence
<220> FEATURE:
<223> OTHER INFORMATION: peptide

<400> SEQUENCE: 26

Arg Ser Ser Gln Ser Leu Glu Asn Ser Asn Gly Asn Thr Tyr Leu Asn
1               5                   10                  15

<210> SEQ ID NO 27
<211> LENGTH: 7
<212> TYPE: PRT
<213> ORGANISM: artificial sequence
<220> FEATURE:
<223> OTHER INFORMATION: peptide

<400> SEQUENCE: 27

Arg Val Ser Asn Arg Phe Ser
1               5

<210> SEQ ID NO 28
<211> LENGTH: 4
```

```
<212> TYPE: PRT
<213> ORGANISM: artificial sequence
<220> FEATURE:
<223> OTHER INFORMATION: peptide

<400> SEQUENCE: 28

Thr Ser Tyr Val
1

<210> SEQ ID NO 29
<211> LENGTH: 121
<212> TYPE: PRT
<213> ORGANISM: artificial sequence
<220> FEATURE:
<223> OTHER INFORMATION: VH mR005-1

<400> SEQUENCE: 29

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Val Asn Trp Met Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Arg Ala Thr Val Thr Ala Asp Lys Ser Ser Ser Thr Ser Tyr
65                  70                  75                  80

Met Gln Phe Ser Ser Leu Thr Ser Glu Asp Ser Ala Val Tyr Phe Cys
                85                  90                  95

Ala Arg Ser Ile Thr Thr Val Val Gly Cys Ala Met Asp Tyr Trp Gly
            100                 105                 110

Gln Gly Thr Ser Val Thr Val Ser Ser
        115                 120

<210> SEQ ID NO 30
<211> LENGTH: 363
<212> TYPE: DNA
<213> ORGANISM: artificial sequence
<220> FEATURE:
<223> OTHER INFORMATION: VH mR005-1

<400> SEQUENCE: 30
caggtccagc tgcagcagtc tggggctgaa ctggtgaggc ctgggtcctc agtgaagatt      60
tcctgtaagg cttctggcta tgcattcagt agctactggg tgaactggat gaagcagagg     120
cctggacagg gacttgagtg gattggacag atttaccctg agatggtga tactaattac      180 aatggaaagt tcaagggtcg agccacagtg actgcagaca atcctccag cacatcctac      240 atgcagttca gcagcctaac atctgaggac tctgcggtct atttctgtgc aagatctatt     300
actacggtgg taggctgtgc tatggactac tggggtcaag gaacctcggt caccgtctcc     360
tca                                                                   363

<210> SEQ ID NO 31
<211> LENGTH: 103
<212> TYPE: PRT
<213> ORGANISM: artificial sequence
<220> FEATURE:
<223> OTHER INFORMATION: peptide
```

<400> SEQUENCE: 31

Asp Ile Gln Met Thr Gln Ser Ser Ala Tyr Leu Ser Val Ser Leu Gly
1               5                   10                  15

Gly Arg Val Thr Ile Thr Cys Lys Ala Ser Asp His Ile Asn Asn Trp
            20                  25                  30

Leu Ala Trp Tyr Gln His Lys Pro Gly Asn Ala Pro Arg Leu Leu Ile
        35                  40                  45

Ser Gly Ala Thr Thr Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Ser Trp Asn Thr Pro Trp
                85                  90                  95

Thr Phe Gly Gly Gly Thr Lys
            100

<210> SEQ ID NO 32
<211> LENGTH: 309
<212> TYPE: DNA
<213> ORGANISM: artificial sequence
<220> FEATURE:
<223> OTHER INFORMATION: VL mR005-1

<400> SEQUENCE: 32

```
gacattcaga tgacccagtc ttctgcctac ctgtctgtat ctctaggagg cagggtcacc      60
attacttgca aggcaagtga ccacattaat aattggttag cctggtatca acataaacca     120
ggaaatgctc ctaggctctt aatatctggt gcaaccactt tggaaactgg ggttccttca     180
agattcagtg gcagtggatc tggaaaggat tacactctca gcattaccag tcttcagact     240
gaagatgttg ctacttatta ctgtcaacag tcttggaata ctccgtggac gttcggtgga     300
ggcaccaag                                                             309
```

<210> SEQ ID NO 33
<211> LENGTH: 120
<212> TYPE: PRT
<213> ORGANISM: artificial sequence
<220> FEATURE:
<223> OTHER INFORMATION: VH mR005-2

<400> SEQUENCE: 33

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Val Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Pro Tyr Tyr Tyr Gly Ser Ser Pro Phe Asp Tyr Trp Gly
            100                 105                 110

Gln Gly Gln Val Thr Val Ser Ser
            115                 120

<210> SEQ ID NO 34
<211> LENGTH: 360
<212> TYPE: DNA
<213> ORGANISM: artificial sequence
<220> FEATURE:
<223> OTHER INFORMATION: VH mR005-2

<400> SEQUENCE: 34

```
gaggttcagc tgcaacagtc tggacctgag ctggtaaagc ctggggcttc agtgaagatg      60
tcctgcaagg cttctggata cacattcact agctatgtta tgcactgggt gaagcagaag     120
cctgggcagg gccttgagtg gattggatat gttaatcctt acaatgatgg tactaagtac     180
aatgagaagt tcaaaggcaa ggccacactg acttcagaca atcctccag  cacagcctac     240
atggagctca gcagcctgac ctctgaggac tctgcggtct attactgtgc aagagggcct     300
tattactacg gtagtagccc ctttgactac tggggccaag gccaggtcac cgtctcctca     360
```

<210> SEQ ID NO 35
<211> LENGTH: 108
<212> TYPE: PRT
<213> ORGANISM: artificial sequence
<220> FEATURE:
<223> OTHER INFORMATION: VL mR005-2

<400> SEQUENCE: 35

```
Asp Ala Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Asn Arg Phe Ser Gly Val Leu
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Thr His Val Pro Pro Thr Phe Gly Ala Gly Thr Lys
            100                 105
```

<210> SEQ ID NO 36
<211> LENGTH: 324
<212> TYPE: DNA
<213> ORGANISM: artificial sequence
<220> FEATURE:
<223> OTHER INFORMATION: VL mR005-2

<400> SEQUENCE: 36

```
gacgctgtga tgacccaaac tccactctcc ctgcctgtca gtcttggaga tcaagcctcc      60
atctcttgca ggtctagtca gagccttgaa aacagtaatg gaaacaccta tttgaactgg     120
tacctccaga aaccaggcca gtctccacag ctcctgatct acagggtttc caaccgattt     180
tctggggtcc tagacaggtt cagtggtagt ggatcaggga cagatttcac actgaaaatc     240
agcagagtgg aggctgagga tttgggagtt tatttctgcc tccaagttac acatgtccct     300
cccacgttcg gtgctgggac caag                                            324
```

<210> SEQ ID NO 37
<211> LENGTH: 214

<212> TYPE: PRT
<213> ORGANISM: artificial sequence
<220> FEATURE:
<223> OTHER INFORMATION: L-IDD001

<400> SEQUENCE: 37

```
Asp Ile Gln Met Thr Gln Ser Pro Ala Ser Leu Ser Ala Ser Val Gly
1               5                   10                  15

Gly Arg Val Thr Ile Thr Cys Lys Ala Ser Gln Ser Ile Asn Asn Trp
            20                  25                  30

Leu Ala Trp Tyr Gln His Lys Pro Gly Lys Ala Pro Lys Leu Leu Ile
        35                  40                  45

Ser Gly Ala Ser Thr Leu Glu Ser Gly Val Pro Ser Arg Phe Ser Gly
    50                  55                  60

Ser Gly Ser Gly Lys Asp Tyr Thr Leu Thr Ile Ser Ser Leu Gln Pro
65                  70                  75                  80

Glu Asp Val Ala Thr Tyr Tyr Cys Gln Gln Ser Trp Asn Thr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 38
<211> LENGTH: 642
<212> TYPE: DNA
<213> ORGANISM: artificial sequence
<220> FEATURE:
<223> OTHER INFORMATION: L-IDD001

<400> SEQUENCE: 38

| | |
|---|---:|
| gacatacaaa tgacacaatc tcccgctagc cttagtgcat cagttggcgg ccgagttacc | 60 |
| atcacatgca aagctagcca aagcatcaac aactggctgg cttggtatca gcacaagccc | 120 |
| ggtaaggcac ctaagctgct catctctggg gcatctactc tggagagtgg tgtgccatcc | 180 |
| cgattttccg ggtctggaag cggaaaggac tatacactga ccatcagcag tttgcaacct | 240 |
| gaagacgttg ccacttatta ctgccaacag tcctggaata cacccctggac cttcggccaa | 300 |
| gggaccaagg tggagatcaa gcgaactgtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag cacccctgacg | 540 |

```
ctgagcaaag cagactacga gaaacacaaa gtctacgcct gcgaagtcac ccatcagggc      600
ctgagctcgc ccgtcacaaa gagcttcaac aggggagagt gt                        642
```

<210> SEQ ID NO 39
<211> LENGTH: 451
<212> TYPE: PRT
<213> ORGANISM: artificial sequence
<220> FEATURE:
<223> OTHER INFORMATION: H-IDD001

<400> SEQUENCE: 39

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Tyr
            20                  25                  30

Trp Val Asn Trp Val Lys Gln Ala Pro Gly Gln Gly Leu Glu Trp Met
        35                  40                  45

Gly Arg Ile Tyr Pro Gly Asp Gly Asp Thr Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Thr Thr Val Val Gly Cys Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Leu Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Glu Glu Gln Tyr Asn Ser Thr Leu
    290                 295                 300

Arg Val Val Ser Leu Leu Thr Val Leu His Gln Asp Trp Leu Asn Gly
305                 310                 315                 320

Lys Glu Tyr Lys Cys Lys Val Ser Asn Ala Ala Leu Pro Ala Pro Ile
                325                 330                 335
```

```
Ala Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Leu
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 40
<211> LENGTH: 1353
<212> TYPE: DNA
<213> ORGANISM: artificial sequence
<220> FEATURE:
<223> OTHER INFORMATION: H-IDD001

<400> SEQUENCE: 40
caagttcaat tggttcagtc tggtgctgag gtaaagaagc ctggaagtag tgtgaaggtg      60
agttgtaaag catctggata cgcttttttcc agttattggg tgaactgggt gaagcaggca     120
cccggtcagg gactggagtg gatgggtagg atctatcccg ggacggaga cacaaactac      180 gctcagaagt tccagggacg cgtgactatt accgccgaca aaagtacttc caccgcatat     240
atggagctgt cttctttgag gtccgaagat accgctgtgt actactgcgc aagatccatc     300
accacagtgg tcggttgcgc tatggattat tggggccagg gtactctcgt gacagtcagt     360
tccgcctcca ccaagggccc atcggtcttc cccctggcac cctcctccaa gagcacctct     420
gggggcacag cggccctggg ctgcctggtc aaggactact tccccgaacc ggtgacggtg     480
tcgtggaact caggcgccct gaccagcggc gtgcacacct tcccggctgt cctacagtcc     540
tcaggactct actccctcag cagcgtcgtg accgtgccct ccagcagctt gggcacccag     600
acctacatct gcaacgtgaa tcacaagccc agcaacacca aggtggacaa gaaagttgag     660
cccaaatctt gtgacaaaac tcacacatgc ccaccgtgcc cagcacctga actcctgggg     720
ggaccgtcag tcttcctctt ccccccaaaa cccaaggaca cctcatgat ctcccggacc     780 cctgaggtca catgcgtggt ggtggacgtg agccacgaag accctgaggt caagttcaac     840
tggtacgtgg acggcgtgga ggtgcataat gccaagacaa agccgccgga ggagcagtac     900
aacagcacgc tccgtgtggt cagcctcctc accgtcctgc accaggactg gctgaatggc     960
aaggagtaca agtgcaaggt ctccaacgca gccctcccag cccccatcgc gaaaaccatc    1020
tccaaagcca aagggcagcc ccgagaacca caggtgtaca ccctgccccc atcccgggat    1080
gagctgacca agaaccaggt cagcctgacc tgcctggtca aaggcttcta tcccagcgac    1140
atcgccgtgg agtgggagag caatgggcag ccggagaaca actacaagac cacgcctctc    1200
gtgctggact ccgacggctc cttcttcctc tacagcaagc tcaccgtgga cagagcagg    1260
```

```
tggcagcagg ggaacgtctt ctcatgctcc gtgatgcatg aggctctgca caaccactac  1320
acgcagaaga gcctctccct gtctccgggt aaa                               1353

<210> SEQ ID NO 41
<211> LENGTH: 6
<212> TYPE: PRT
<213> ORGANISM: artificial sequence
<220> FEATURE:
<223> OTHER INFORMATION: peptide

<400> SEQUENCE: 41

Gln Ser Ile Asn Asn Trp
1               5

<210> SEQ ID NO 42
<211> LENGTH: 11
<212> TYPE: PRT
<213> ORGANISM: artificial sequence
<220> FEATURE:
<223> OTHER INFORMATION: peptide

<400> SEQUENCE: 42

Lys Ala Ser Gln Ser Ile Asn Asn Trp Leu Ala
1               5                   10

<210> SEQ ID NO 43
<211> LENGTH: 3
<212> TYPE: PRT
<213> ORGANISM: artificial sequence
<220> FEATURE:
<223> OTHER INFORMATION: peptide

<400> SEQUENCE: 43

Gly Ala Ser
1

<210> SEQ ID NO 44
<211> LENGTH: 7
<212> TYPE: PRT
<213> ORGANISM: artificial sequence
<220> FEATURE:
<223> OTHER INFORMATION: peptide

<400> SEQUENCE: 44

Gly Ala Ser Thr Leu Glu Thr
1               5
```